United States Patent
Packouz et al.

(10) Patent No.: US 12,343,225 B2
(45) Date of Patent: Jul. 1, 2025

(54) APPARATUS FOR DENTAL IRRIGATION

(71) Applicant: EHT, LLC, Sarasota, FL (US)

(72) Inventors: Elimelech Packouz, Sarasota, FL (US); Ralf Raud, Sarasota, FL (US)

(73) Assignee: EHT, LLC, Sarasoto, FL (US)

(*) Notice: Subject to any disclaimer, the term of this patent is extended or adjusted under 35 U.S.C. 154(b) by 0 days.

(21) Appl. No.: 18/749,982

(22) Filed: Jun. 21, 2024

(65) Prior Publication Data

US 2024/0341934 A1    Oct. 17, 2024

Related U.S. Application Data

(63) Continuation of application No. 18/605,708, filed on Mar. 14, 2024, which is a continuation of application (Continued)

(51) Int. Cl.
*A61C 17/02* (2006.01)
*A46B 9/04* (2006.01)
(Continued)

(52) U.S. Cl.
CPC .......... *A61C 17/0211* (2013.01); *A46B 9/045* (2013.01); *A46B 11/0006* (2013.01); (Continued)

(58) Field of Classification Search
CPC ................ A61C 17/02; A61C 17/0211; A61C 17/028; A61C 17/228; A61C 17/16; (Continued)

(56) References Cited

U.S. PATENT DOCUMENTS 3,489,141 A    1/1970    Warren, Jr.
3,504,666 A    4/1970    Vireno
(Continued)

FOREIGN PATENT DOCUMENTS

BR    112020016408-9    12/2020
CN    212547223 U       2/2021
(Continued)

OTHER PUBLICATIONS

International Search Report and Written Opinion dated Apr. 15, 2019 cited in Application No. PCT/US19/17897, 9 pgs.
(Continued)

*Primary Examiner* — Bradley H Philips
*Assistant Examiner* — Savannah L Gabriel
(74) *Attorney, Agent, or Firm* — BEKIARES ELIEZER LLP

(57) ABSTRACT

An apparatus may include one or more manifolds, each including a shell having an inner portion and an outer portion. Each shell may have a first set of outlets in a first wall and a second set of outlets in a second wall that approximately faces the first wall. Each manifold is shaped to accommodate a tooth. A rotating inlet joint, having an inlet channel and a rotating joint, may enable fluid flow into each manifold from the inlet channel at any angle relative to an axis of rotation defined by the rotating joint. In each manifold, the first set of outlets and the second set of outlets are oriented towards a tooth and/or gums associated with the tooth. The inner portion and the outer portion of each shell cooperate to direct fluid flow substantially horizontal to, and then substantially perpendicular to, the fluid flow exiting the inlet channel.

20 Claims, 28 Drawing Sheets

Related U.S. Application Data

No. 17/196,931, filed on Mar. 9, 2021, now Pat. No. 11,931,217, which is a continuation of application No. 16/901,495, filed on Jun. 15, 2020, now Pat. No. 10,945,593, which is a continuation of application No. 16/611,142, filed as application No. PCT/US2019/017897 on Feb. 13, 2019, now Pat. No. 11,399,705.

(60) Provisional application No. 62/629,904, filed on Feb. 13, 2018.

(51) Int. Cl.
| | |
|---|---|
| *A46B 11/00* | (2006.01) |
| *A61B 1/06* | (2006.01) |
| *A61B 1/24* | (2006.01) |
| *A61B 5/00* | (2006.01) |
| *A61C 9/00* | (2006.01) |
| *A61C 17/028* | (2006.01) |
| *A61H 13/00* | (2006.01) |

(52) U.S. Cl.
CPC .............. *A61B 1/06* (2013.01); *A61B 1/24* (2013.01); *A61B 5/0088* (2013.01); *A61C 9/0053* (2013.01); *A61C 17/028* (2013.01); *A46B 2200/1026* (2013.01); *A46B 2200/108* (2013.01); *A61H 13/005* (2013.01)

(58) Field of Classification Search
CPC ............ A61C 9/0053; A46B 2200/108; A46B 2200/1026; A46B 9/045; A46B 11/0006; A61B 1/06; A61B 5/0088; A61B 1/24; A61H 13/005

See application file for complete search history.

(56) References Cited

U.S. PATENT DOCUMENTS

| | | | |
|---|---|---|---|
| 4,223,417 A | 9/1980 | Solow | |
| 5,027,463 A | 7/1991 | Daub | |
| 5,570,709 A | 11/1996 | Haddad et al. | |
| 5,800,367 A | 9/1998 | Saxer et al. | |
| 5,842,249 A | 12/1998 | Sato | |
| 6,625,834 B2 | 9/2003 | Dean | |
| 6,862,771 B1 | 3/2005 | Muller | |
| 9,022,961 B2 | 5/2015 | Fougere et al. | |
| 9,259,301 B2 | 2/2016 | Zhadanov et al. | |
| 9,572,641 B2 | 2/2017 | Fougere et al. | |
| 9,655,704 B2 | 5/2017 | Beckman | |
| 9,776,317 B1 | 10/2017 | Jackson | |
| 10,098,717 B2 | 10/2018 | Bergheim et al. | |
| 10,945,593 B1 | 3/2021 | Packouz et al. | |
| 11,399,705 B2 | 8/2022 | Packouz et al. | |
| 11,931,217 B2 | 3/2024 | Packouz et al. | |
| 2002/0152563 A1 | 10/2002 | Sato | |
| 2009/0208898 A1 | 8/2009 | Kaplan | |
| 2011/0033823 A1 | 2/2011 | Gersh et al. | |
| 2011/0113576 A1 | 5/2011 | Yankell | |
| 2011/0191971 A1* | 8/2011 | Zeng .................... | A46B 5/0054 15/167.2 |
| 2012/0064480 A1 | 3/2012 | Hegemann | |
| 2012/0077143 A1 | 3/2012 | Fougere et al. | |
| 2012/0077144 A1* | 3/2012 | Fougere ............ | A61C 17/0211 433/82 |
| 2013/0061412 A1 | 3/2013 | Vashi | |
| 2014/0325771 A1 | 11/2014 | Arnoux et al. | |
| 2015/0140503 A1 | 5/2015 | Bergheim et al. | |
| 2015/0250571 A1 | 9/2015 | Oelgiesser | |
| 2016/0022398 A1 | 1/2016 | Vetter et al. | |
| 2017/0007384 A1 | 1/2017 | Wagner | |
| 2017/0056143 A1 | 3/2017 | Hyun | |
| 2017/0239028 A1 | 8/2017 | Baek | |
| 2017/0347953 A1 | 12/2017 | Suri et al. | |
| 2018/0140402 A1 | 5/2018 | Chu | |
| 2018/0295979 A1 | 10/2018 | Miller et al. | |
| 2019/0000599 A1 | 1/2019 | Hanuschik et al. | |
| 2020/0077875 A1 | 3/2020 | Packouz et al. | |
| 2020/0093255 A1 | 3/2020 | Mediratta et al. | |
| 2020/0121428 A1 | 4/2020 | Pai et al. | |
| 2021/0212558 A1 | 7/2021 | Packouz et al. | |
| 2022/0378562 A1 | 12/2022 | Packouz et al. | |

FOREIGN PATENT DOCUMENTS

| | | | | |
|---|---|---|---|---|
| DE | 3337054 A1 | 10/1985 | | |
| DE | 4029369 | * 9/1990 | ......... | A61C 17/0202 |
| DE | 4029369 A1 | 3/1992 | | |
| DE | 202008016469 U1 | 5/2009 | | |
| EP | 1733699 A1 | 12/2006 | | |
| JP | 2003-319834 A | 11/2003 | | |
| JP | 2005-185397 A | 7/2005 | | |
| JP | 2008-515575 A | 5/2008 | | |
| JP | 2009-502214 A | 1/2009 | | |
| JP | 2013-500783 A | 1/2013 | | |
| JP | 2021513438 | 5/2021 | | |
| KR | 10-1791005 B1 | 10/2017 | | |
| WO | 9400076 | 1/1994 | | |
| WO | 2019160989 A1 | 8/2019 | | |

OTHER PUBLICATIONS

Chinese Notification for Making Rectification dated Jul. 20, 2020 cited in Application No. 201990000206.0 with English language Comments, 4 pgs.
U.S. Non-Final Office Action dated Aug. 21, 2020 cited in U.S. Appl. No. 16/901,495, 30 pgs.
International Preliminary Report on Patentability dated Aug. 27, 2020 cited in Application No. PCT/US19/17897, 8 pgs.
U.S. Non-Final Office Action dated Apr. 22, 2021 cited in U.S. Appl. No. 16/611,142, 57 pgs.
U.S. Final Office Action dated Oct. 28, 2021 cited in U.S. Appl. No. 16/611,142, 12 pgs.
Extended European Search Report dated Jan. 26, 2022 cited in Application No. 19753864.8, 7 pgs.
Indian First Examination Report dated Jul. 12, 2022 cited in Application No. 202027039538, 7 pgs.
Japanese Notification of Reasons for Refusal dated Mar. 9, 2023 cited in Application No. 2020-564823, with English Translation, 10 pgs.
Indonesian Office Action dated Apr. 13, 2023 cited in Application No. P00202006635, 6 pgs.
Australian Examination Report No. 1 dated Nov. 29, 2023 cited in Application No. 2019222718, 3 pgs.
U.S. Non-Final Office Action dated Apr. 10, 2025 cited in U.S. Appl. No. 18/605,708, 45 pgs.

* cited by examiner

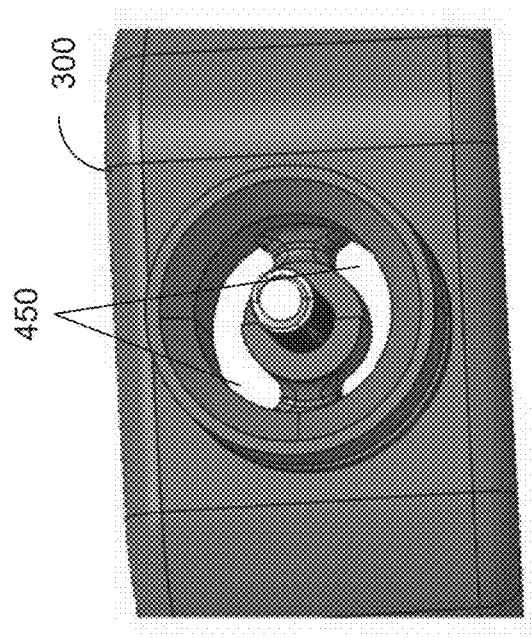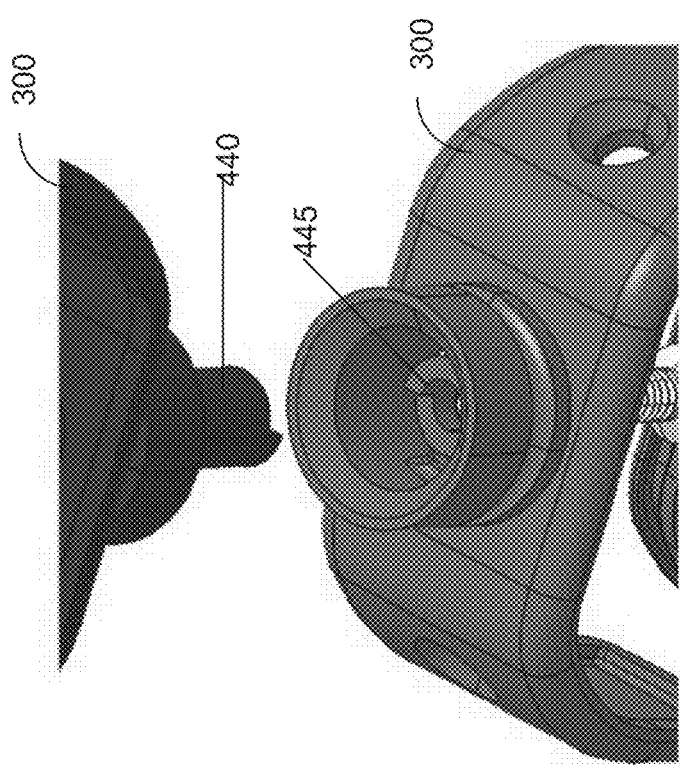
FIG. 9

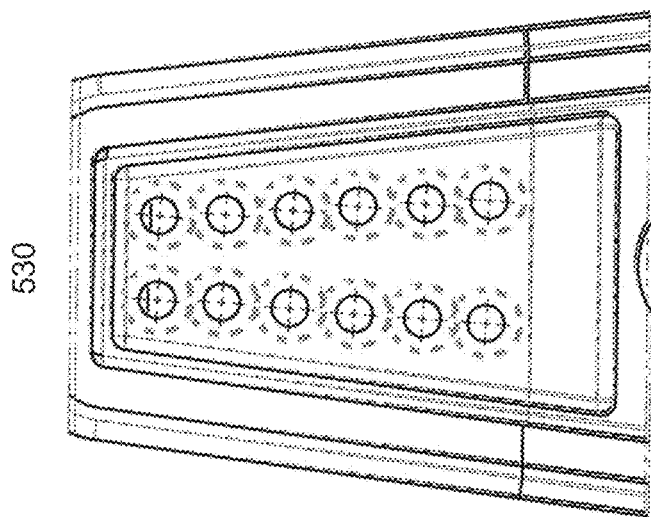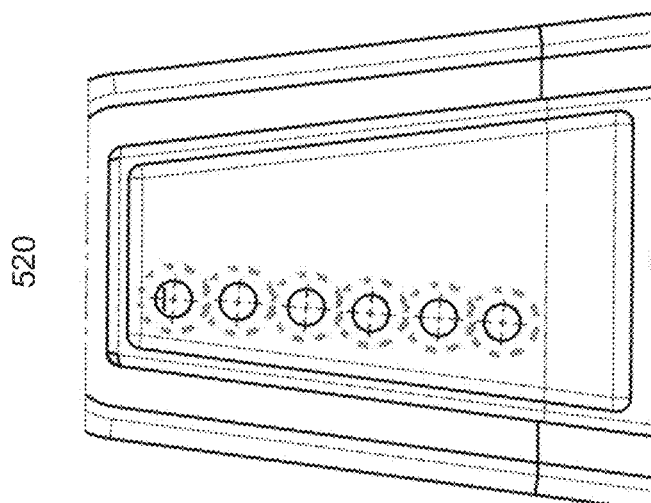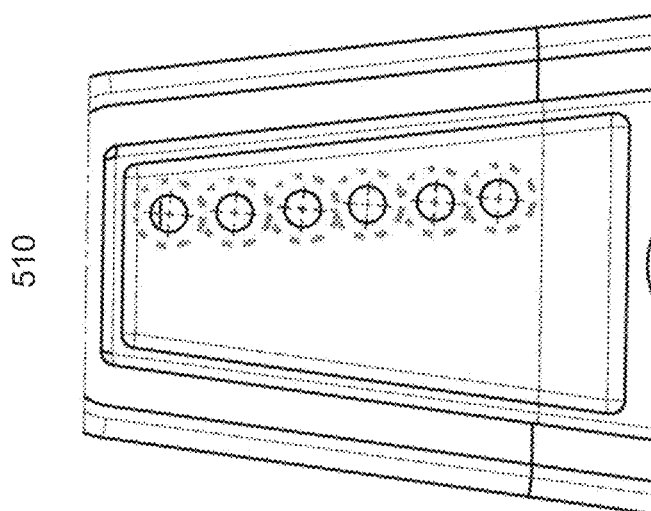
FIG. 18

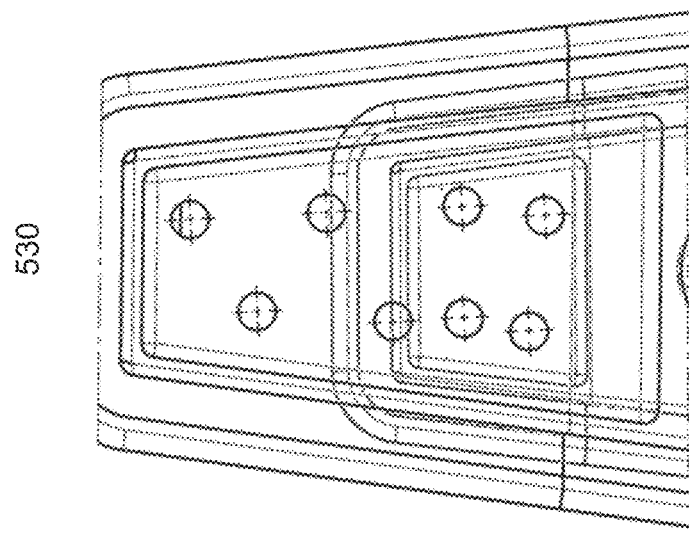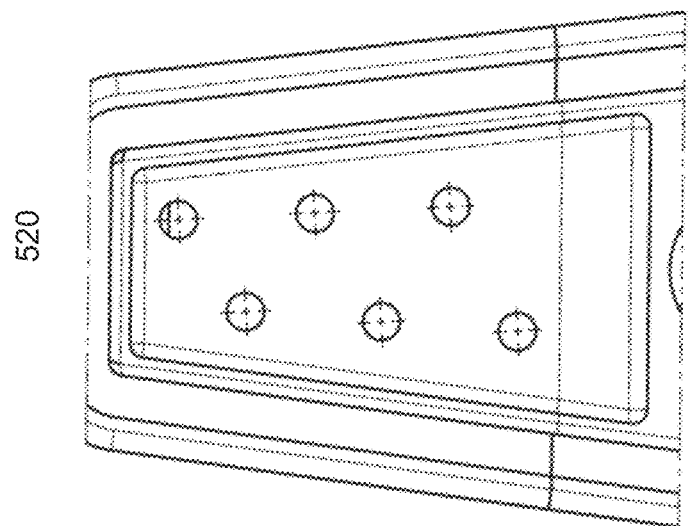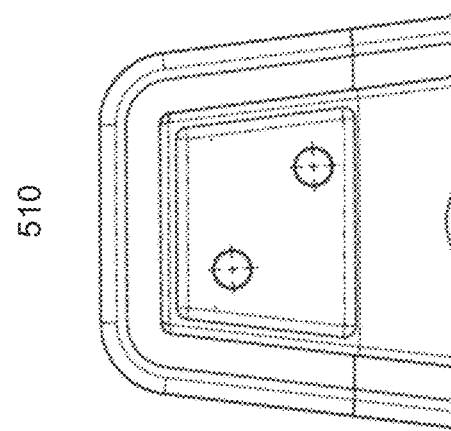
FIG. 19

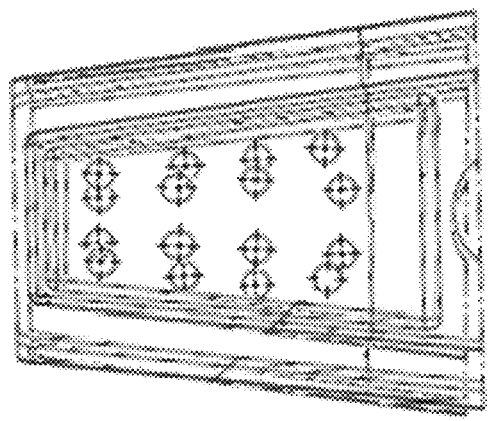
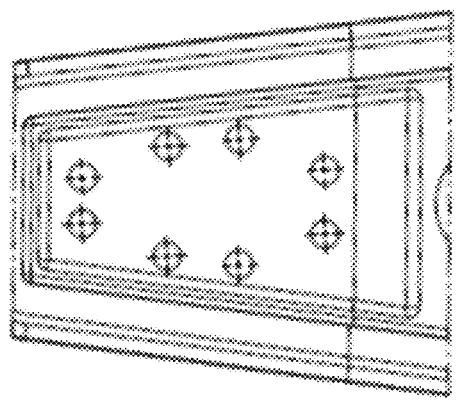
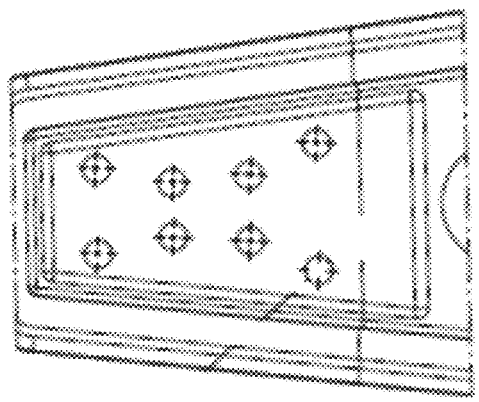
FIG. 20

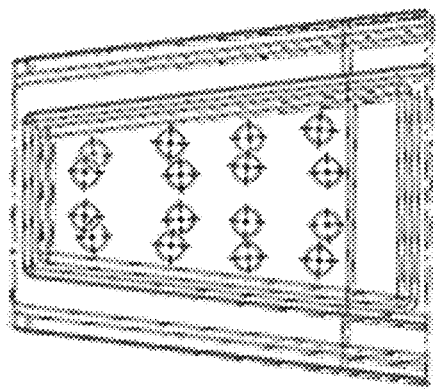
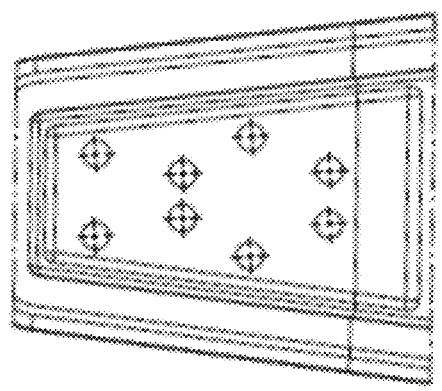
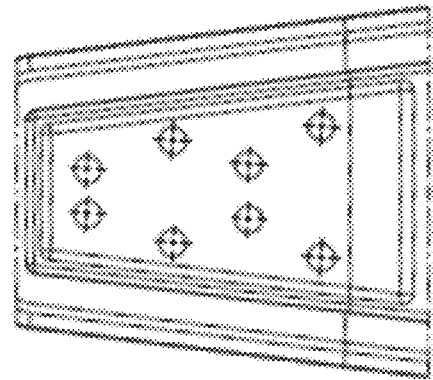
FIG. 21

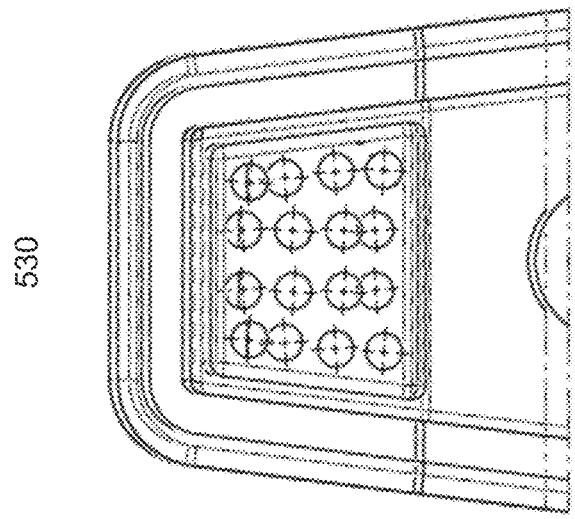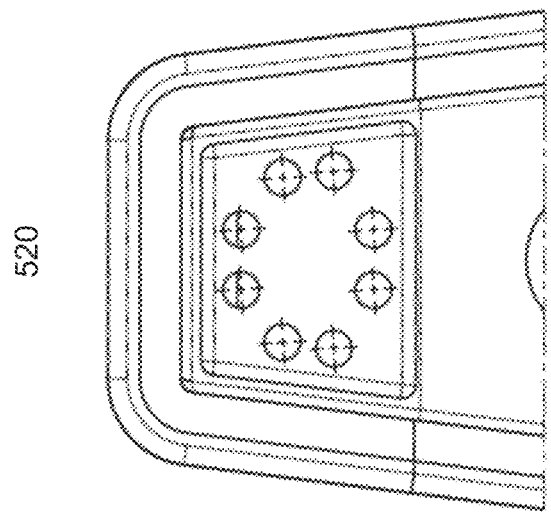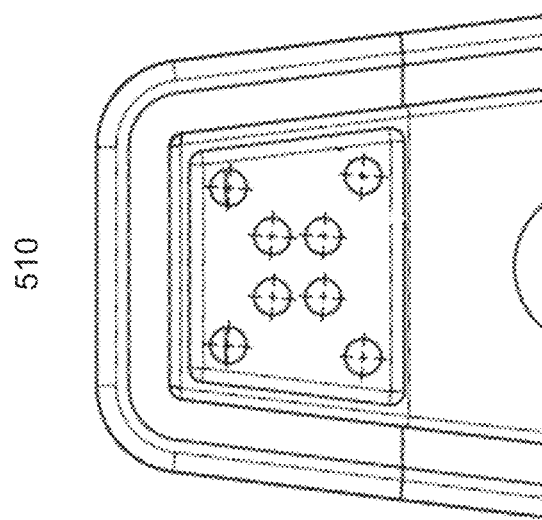
FIG. 22

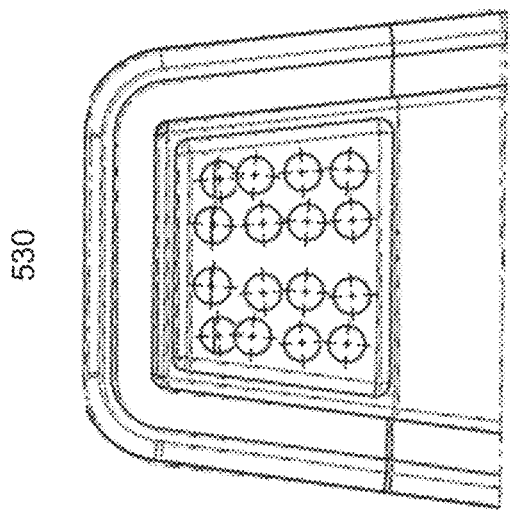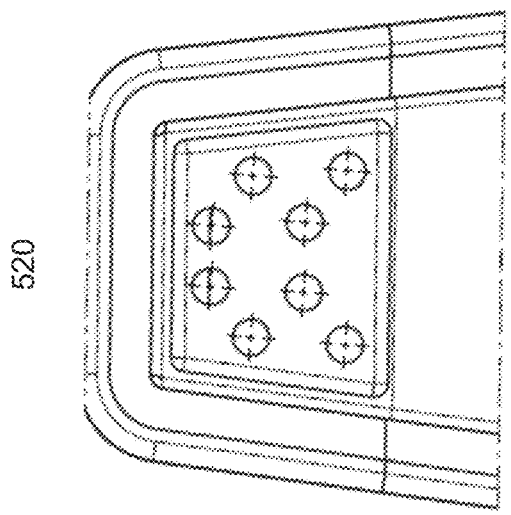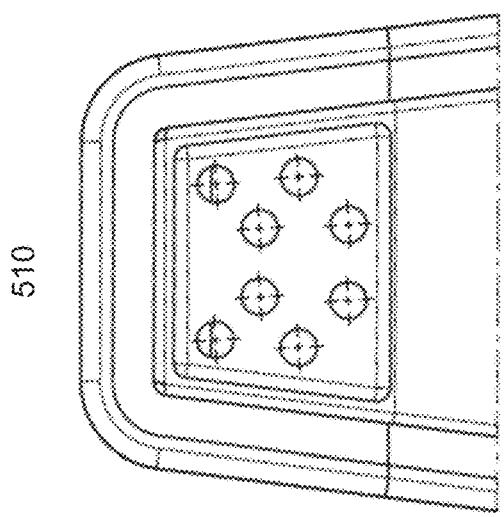
FIG. 23

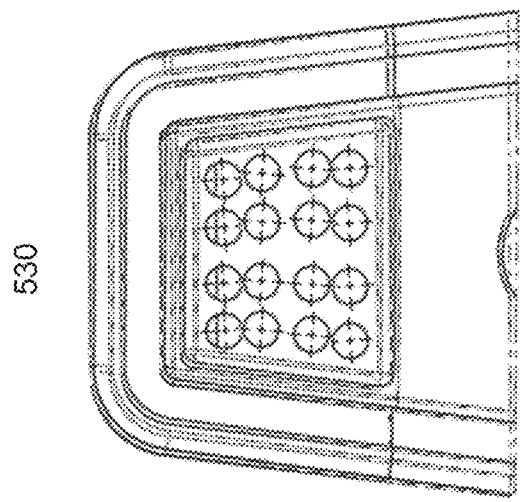
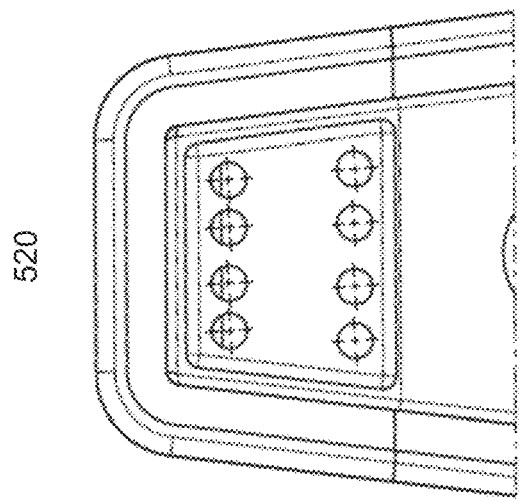
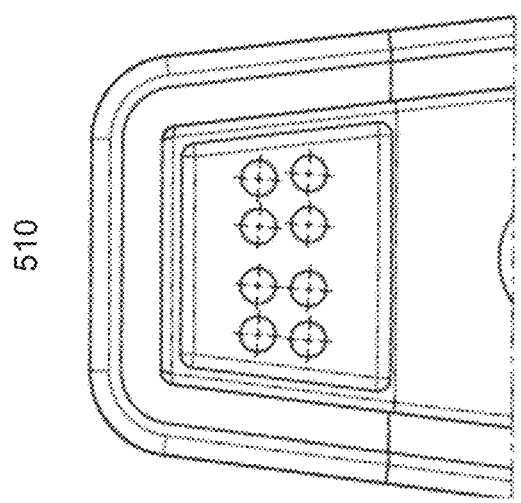
FIG. 24

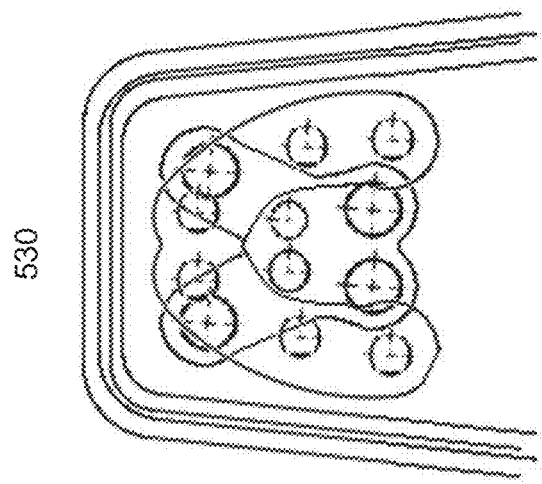
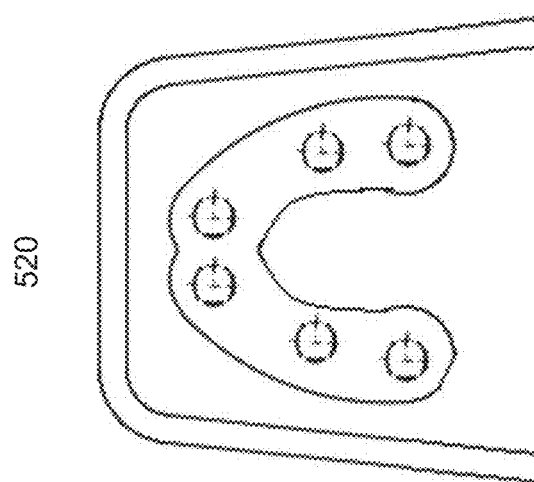
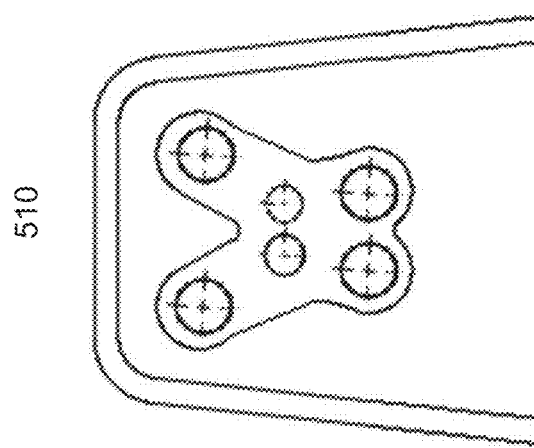
FIG. 25

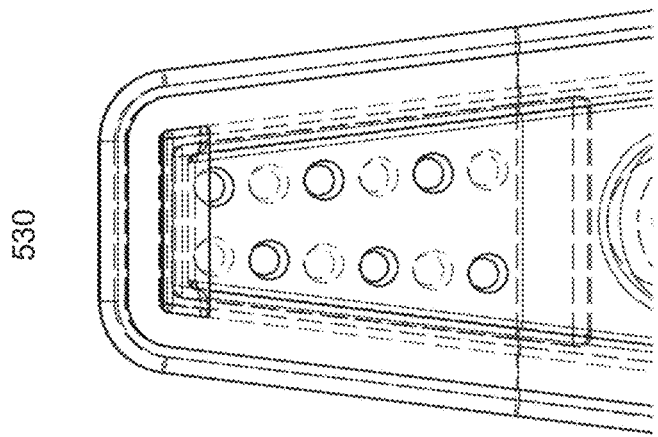
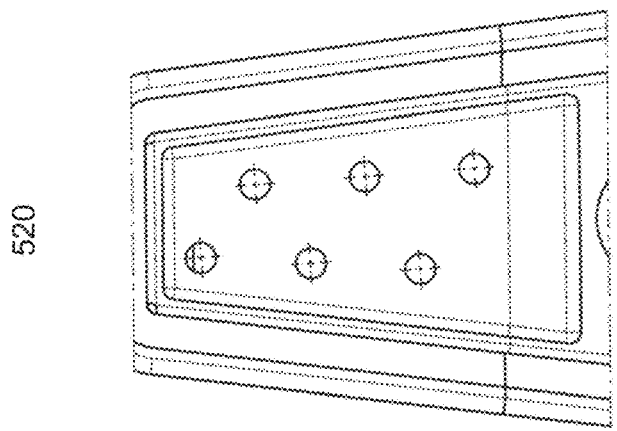
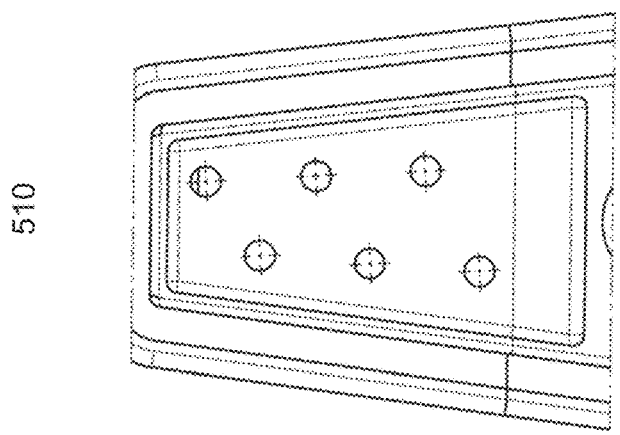
FIG. 26

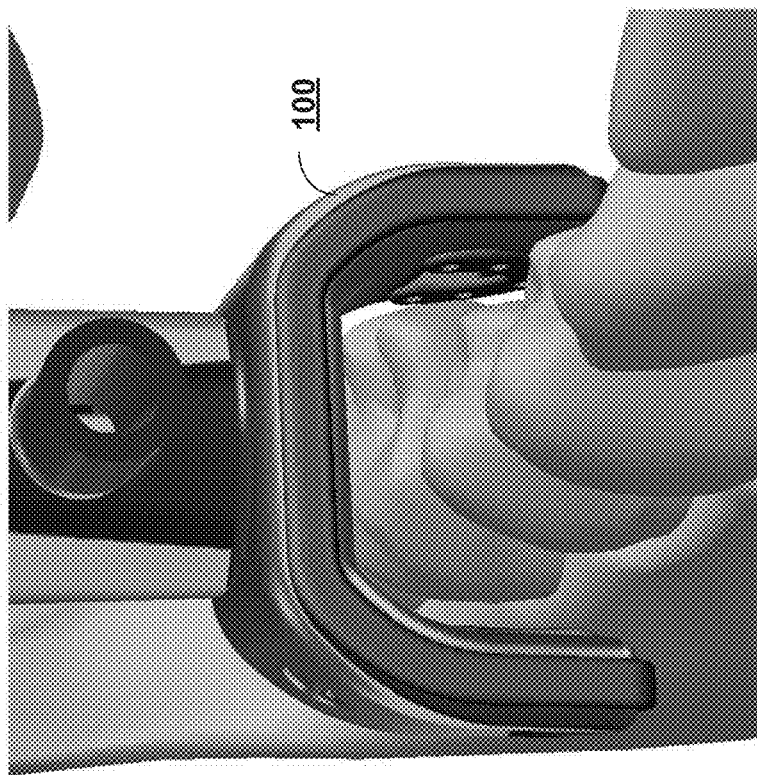
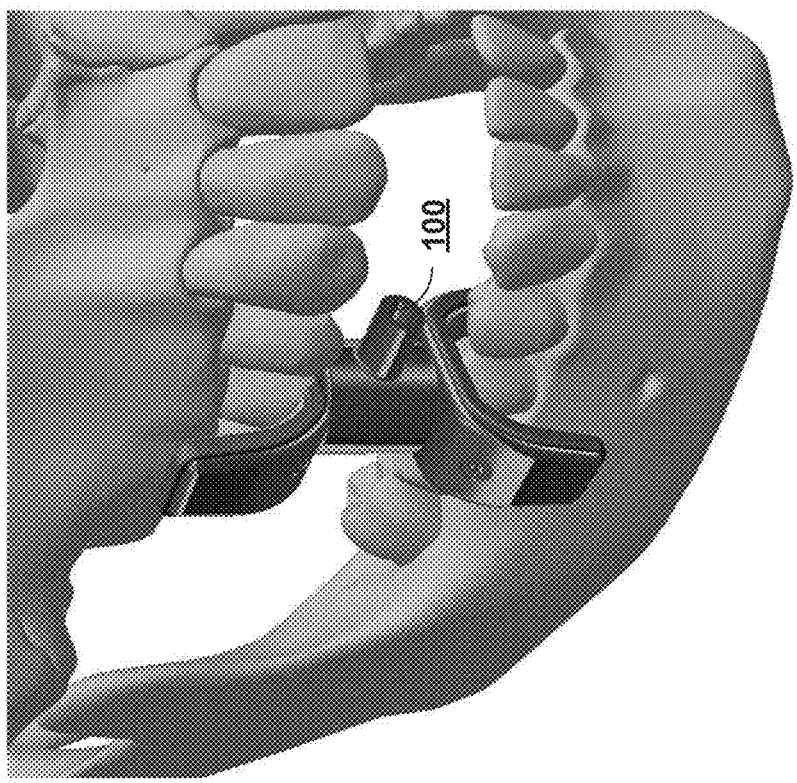
FIG. 27

APPARATUS FOR DENTAL IRRIGATION

RELATED APPLICATIONS

The present application is a Continuation of U.S. application Ser. No. 18/605,708 filed on Mar. 14, 2024, which is a Continuation of U.S. application Ser. No. 17/196,931 filed on Mar. 9, 2021, which issued on Mar. 19, 2024 as U.S. Pat. No. 11,931,217, which is a Continuation of U.S. application Ser. No. 16/901,495 filed on Jun. 15, 2020, which issued on Mar. 16, 2021 as U.S. Pat. No. 10,945,593, which is a Continuation of U.S. application Ser. No. 16/611,142 filed on Nov. 5, 2019, which issued on Aug. 2, 2022 as U.S. Pat. No. 11,399,705, which is a National Stage filing under 35 U.S.C. § 371 of International Application No. PCT/US2019/017897 filed on Feb. 13, 2019, which claims benefit under the provisions of 35 U.S.C. § 119 (e) of U.S. Provisional Application No. 62/629,904 filed on Feb. 13, 2018, and having inventors in common, which are incorporated herein by reference in its entirety.

It is intended that the referenced application may be applicable to the concepts and embodiments disclosed herein, even if such concepts and embodiments are disclosed in the referenced application with different limitations and configurations and described using different examples and terminology.

FIELD OF DISCLOSURE

The present disclosure generally relates to dental hygiene methods, systems and devices.

BACKGROUND

Clean teeth and impeccable dental hygiene are important. Good oral and dental hygiene can help prevent bad breath, tooth decay and gum disease, as well as improve overall health. Furthermore, good oral and dental hygiene has been linked to overall physical wellbeing. The conventional strategy is to brush a person's teeth and use dental floss or a toothpick at least twice daily. This often causes problems because the conventional strategy does not allow for pristine dental cleaning to be performed effectively and efficiently. There is a need for a more effective and efficient solution.

BRIEF OVERVIEW

An apparatus for accurate, precise, effective, and convenient dental cleaning and irrigation may be provided by the present disclosure. This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

An apparatus for dental irrigation may be provided to project fluid directly onto the surfaces of, and the interproximal spaces between, a user's teeth and gum-line. The apparatus may comprise two hollow U-shaped manifolds having orifices located on their interior faces used as fluid jets. The U-Shaped manifolds may be connected, at a central point of reflection, by a rotating inlet joint which supplies the fluid flow. When placed in the user's mouth, an apparatus consistent with the present disclosure may be designed to receive the top and bottom sets of teeth in each corresponding U-shaped manifold, with orifices configured to provide fluid jets aligned towards the lingual and buccal side of the user's teeth. The orifices may be staggered to provide staggered fluid flow. A user's teeth may be cleaned with a controlled fluid flow by moving the apparatus in a sweeping motion between each set of rear molars.

Still consistent with embodiments of the present disclosure, an apparatus for dental irrigation may comprise:
a first manifold having a first plurality of outlet holes laid out on a first wall of the first manifold and a second plurality of outlet holes laid out on a second wall of the first manifold, wherein the first wall of the first manifold approximately faces the second wall of the first manifold, wherein the first plurality of outlet holes are approximately oriented towards the second plurality of outlet holes,
wherein the first plurality of outlet holes are at a first height, the second plurality of outlet holes are at a second height that is different from the first height such that the first plurality of outlet holes and the second plurality of outlet holes of the first manifold are vertically offset,
wherein the first manifold further comprises:
a first inner shell,
a first outer shell, and
a first soft membrane layer disposed between the first inner shell and the first outer shell, and
a rotating inlet joint configured to enable a flow of a fluid into the first manifold from an inlet channel at any angle of rotation.

In yet further embodiments, an apparatus for dental irrigation designed to project fluid directly onto surfaces of, and interproximal spaces between, a user's teeth and gum-line, comprising:
a first manifold segment comprising:
a first arm of the first manifold segment having a first plurality of outlet holes, the first plurality of outlet holes providing an opening into a hollow interior of the first arm of the first manifold segment,
a second arm of the second manifold segment having a second plurality of outlet holes, the second plurality of outlet holes providing an opening into a hollow interior of the second arm of the first manifold segment,
wherein the first plurality of outlet holes are at a first height, the second plurality of outlet holes are at a second height that is different from the first height such that the first plurality of outlet holes and the second plurality of outlet holes are vertically offset,
wherein the first manifold segment further comprises:
a first inner shell,
a first outer shell, and
a first soft membrane layer disposed between the first inner shell and the first outer shell, and
a rotating inlet segment configured to enable a flow of a fluid into the first manifold segment from an inlet channel at any angle of rotation.

In some aspects, the techniques described herein relate to an apparatus for dental irrigation, the apparatus including a first manifold including a first shell having an inner portion and an outer portion, the first shell having a first set of one or more outlets in a first wall and a second set of one or more outlets in a second wall, wherein the first wall approximately faces the second wall, and wherein at least a portion of the first manifold is shaped to accommodate a tooth. A second manifold includes a second shell having an inner portion and an outer portion, the second shell having a third set of one or more outlets in a third wall and a fourth set of one or more outlets in a fourth wall, wherein the third wall approximately faces the fourth wall, and wherein at least a portion of the second manifold is shaped to accommodate a tooth. A rotating inlet joint includes an inlet channel and a rotating joint, the rotating inlet joint being configured to enable a flow of a fluid into the first manifold and the second manifold from the inlet channel at any angle of rotation about an axis of rotation defined by the rotating joint. The first set of one or more outlets and the second set of one or more outlets are oriented towards a tooth accommodated by the first manifold and gums associated with the tooth. The third set of one or more outlets and the fourth set of one or more outlets are oriented towards a tooth accommodated by the second manifold and gums associated with the tooth. The inner portion and the outer portion of the first shell cooperate to direct fluid flow substantially horizontal to the fluid flow exiting the inlet channel, and then substantially perpendicular to the fluid flow exiting the inlet channel. The inner portion and the outer portion of the second shell cooperate to direct fluid flow substantially horizontal to the fluid flow exiting then inlet channel, and then substantially perpendicular to the fluid flow exiting the inlet channel.

In some aspects, the techniques described herein relate to an apparatus for dental irrigation, the apparatus including a first manifold having a first set of one or more outlets laid out on a first wall of the first manifold and a second set of one or more outlets laid out on a second wall of the first manifold, and at least one first inlet, at least a portion of the first manifold being shaped to accommodate a tooth. A second manifold has a third set of one or more outlets laid out on a first wall of the second manifold and a fourth set of one or more outlets laid out on a second wall of the second manifold, and at least one second inlet, at least a portion of the second manifold being shaped to accommodate a tooth. A rotating inlet joint includes an inlet channel to receive fluid and a rotating joint to channel the fluid in substantially opposing directions into the first manifold through the at least one first inlet, and into the second manifold through the at least one second inlet, wherein the rotating inlet joint. The first manifold and the second manifold are positioned so as to approximately align with an approximately central vertical axis of common symmetry, and reflect about an approximately central horizontal axis of symmetry, such that the first manifold and the second manifold are positioned at opposite sides of the rotating inlet joint and are oriented in opposite directions. The first manifold and the second manifold rotate about the axis of common symmetry. The rotating inlet joint is configured to rotate about the axis of common symmetry, and the angle of rotation of the rotating inlet joint about the axis of common symmetry impacts a property of the fluid flow to a user's teeth and associated gums.

In some aspects, the techniques described herein relate to an apparatus for dental irrigation, the apparatus including a first manifold including a first shell having an inner portion and an outer portion, the first shell having a first set of one or more outlets laid out on a first wall and a second set of one or more outlets laid out on a second wall, wherein the first wall approximately faces the second wall, wherein at least a portion of the first manifold further is shaped to accommodate a tooth. A rotating inlet joint is configured to enable a flow of a fluid into the first manifold from an inlet channel at any angle of rotation about an axis of rotation. The inner portion and the outer portion of the first shell cooperate to direct the fluid flow substantially perpendicularly to the fluid flow exiting the inlet channel, and then substantially parallel to the fluid flow exiting the inlet channel, then substantially perpendicularly again.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the Applicants. The Applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings:

FIG. 9 illustrates an anti-rotate feature internal attachment that prevents misalignment of the upper and lower U-shaped manifolds, as well as the fluid flow openings on the lower section of the U-shaped manifolds, both consistent with various embodiments of the present disclosure;

FIG. 18 illustrates another example of non-intersecting fluid jet positions for the apparatus consistent with various embodiments of the present disclosure;

FIG. 19 illustrates an example of non-intersecting fluid jet positions for the apparatus with different buccal and lingual side heights;

FIG. 20 illustrates yet another example of non-intersecting fluid jet positions for the apparatus consistent with various embodiments of the present disclosure;

FIG. 21 illustrates an alternative example of non-intersecting fluid jet positions for the apparatus consistent with various embodiments of the present disclosure;

FIG. 22 illustrates another alternative example of non-intersecting fluid jet positions for the apparatus consistent with various embodiments of the present disclosure;

FIG. 23 illustrates yet another alternative non-intersecting fluid jet positions for the apparatus consistent with various embodiments of the present disclosure;

FIG. 24 illustrates yet another example of non-intersecting fluid jet positions for the apparatus consistent with various embodiments of the present disclosure;

FIG. 25 illustrates yet another example of non-intersecting fluid jet positions for the apparatus consistent with various embodiments of the present disclosure;

FIG. 26 illustrates yet another example of non-intersecting fluid jet positions for the apparatus consistent with various embodiments of the present disclosure;

FIG. 27 illustrates an embodiment of the apparatus consistent with various embodiments of the present disclosure in relation to a typical jaw.

DETAILED DESCRIPTION

Figure 1:
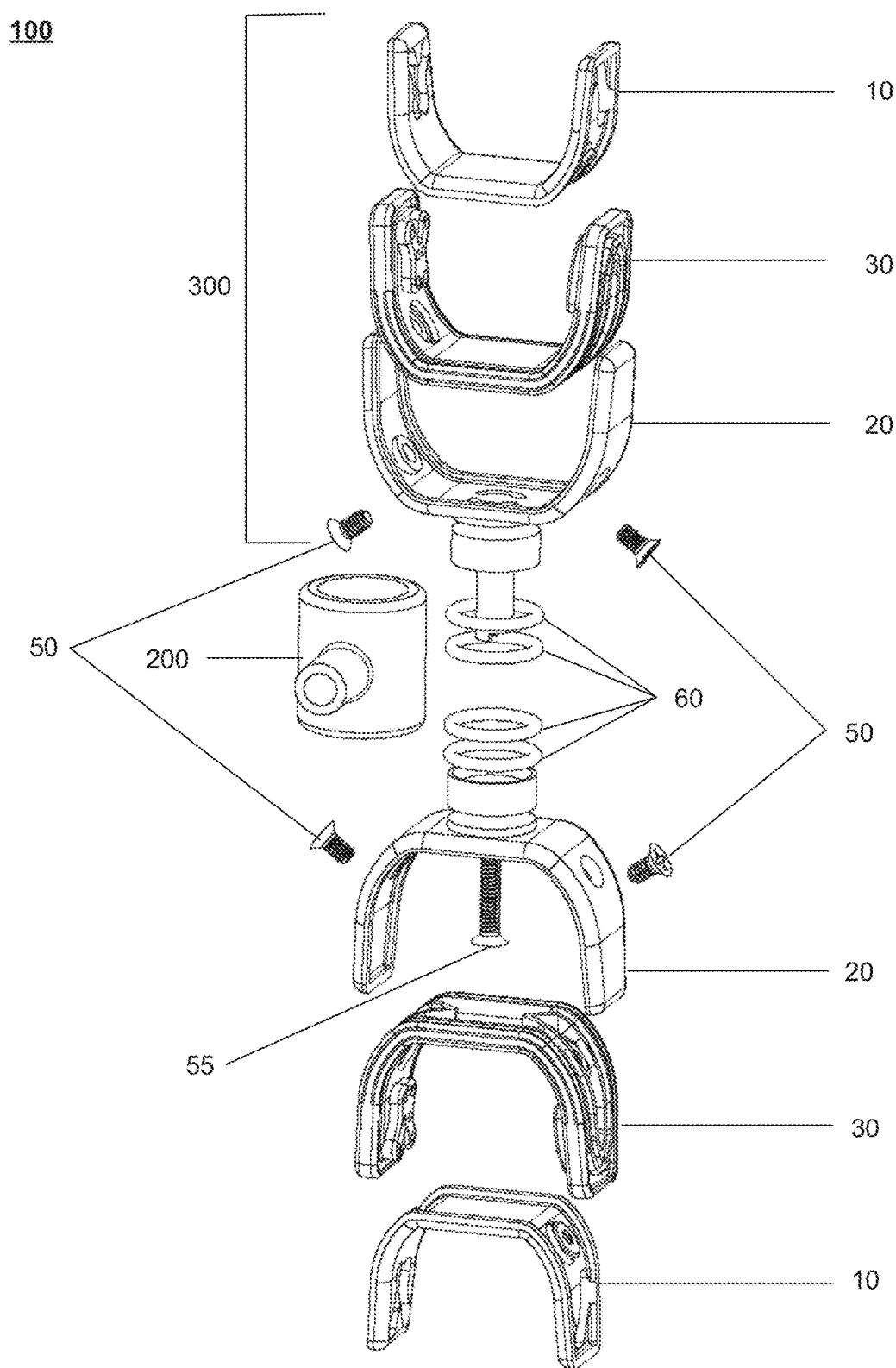
FIG. 1 illustrates a general overview of an apparatus assembly consistent with the present disclosure, broken down into individual components.

As a preliminary matter, it will readily be understood by a person having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term-differs in any way from any particular dictionary definition of such term, it is intended that the meaning of the term as understood by the ordinary artisan should prevail.

Regarding applicability of 35 U.S.C. § 112, 16, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subject matter disclosed under the header.

The present disclosure includes many aspects and features. Moreover, while many aspects and features relate to, and are described in, the context of dental hygiene, embodiments of the present disclosure are not limited to use only in this context.

Consistent with embodiments of the present disclosure, an apparatus for accurate, efficient, and convenient dental cleaning and irrigation may be provided. This overview is provided to introduce a selection of concepts in a simplified form that are further described below. This overview is not intended to identify key features or essential features of the claimed subject matter. Nor is this overview intended to be used to limit the claimed subject matter's scope. The apparatus for accurate, efficient, and convenient dental cleaning and irrigation may be used by individuals, dental practitioners, and/or companies to perform dental irrigation, improve dental hygiene, clean teeth, remove plaque, massage gums, kill bacteria and monitor dental state.

Both the foregoing overview and the following detailed description provide examples that are only used for illustrative purposes. Accordingly, the foregoing overview and the ensuing detailed description should not be considered to be restrictive. Further, features or variations may be provided in addition to those set forth herein. For example, embodiments may be directed to various feature combinations and sub-combinations described herein.

Although the stages and/or components and components illustrated by the figures are disclosed in a particular order, it should be understood that the order is disclosed for illustrative purposes only. Stages and/or components may be combined, separated, reordered, and various intermediary stages and/or components may exist. Accordingly, it should be understood that the various stages and/or components illustrated within the flow chart may be, in various embodiments, performed in arrangements that differ from the ones illustrated. Moreover, various stages and/or components may be added or removed from the figures without altering or deterring from the fundamental scope of the depicted methods and systems disclosed herein. Ways to implement the stages and/or components of the apparatus will be described in greater detail below.

I. OVERVIEW

An apparatus consistent with embodiments of the present disclosure may be designed such that a controlled pressure flow of fluid is directly projected onto teeth surfaces, interproximal spaces, and gum line of a user's mouth. The apparatus may comprise two hollow manifold components having holes located on the interior faces of each manifold, and a rotating inlet joint attaching the two manifolds at a central point of reflection. The manifolds may be in a variety of different geometric configurations, such as, but not limited to, U-shaped, parabolic, or rectangular. In embodiments disclosing a parabolic shape, the term parabolic may be taken to mean that the shape of the interior face of the manifold can be approximated with an even order polynomial function.

For illustrative purposes, the manifold may be described herein as a U-shaped manifold. Each U-shaped manifold may be embodied such that it fits around a user's corresponding upper and lower teeth. Although various embodiment disclosed herein mention a symmetrical configuration for the apparatus, and each corresponding manifold, it should be understood that symmetry may only be approximate, and that the configuration of the manifolds and apparatus may be ergonomically designed to fit into a user's mouth, which includes asymmetry from the buccal to lingual sides, and design accommodations for overbite and/or underbite.

Furthermore, some embodiments of the manifold 300 consistent with the present disclosure may comprise a different component, as well as different number of components. For example, the manifold 300 may comprise a single piece mold or the inner shell 10 and outer shell 20 without a membrane layer 30. Moreover, although embodiments herein describe two manifolds configured together, it should be understood that the apparatus may be comprised of a single part or construction. Accordingly, the break-down of the apparatus into parts is provided for illustrative purposes and contemplate a single part construction.

The apparatus may provide fluid jets aligned towards the lingual and buccal side of the user's teeth for staggered fluid flow. A user's teeth may be cleaned by moving the apparatus over the teeth in a sweeping manner such that a sweep of the manifold from one rear molar to the other will ensure all of the gum line and every interproximal space is cleaned with the aforementioned fluid jets.

It should be understood that the present specification and figures disclose only some embodiments of the apparatus, and that other embodiments of the apparatus consistent with the present disclosure may be anticipated with the present disclosure. Varying embodiments of the apparatus could have varying components, as well as a varying number and combination of components.

FIG. 1 illustrates an apparatus consistent with the present disclosure, broken down into individual components. The apparatus may comprise two hollow U-shaped manifolds 300, wherein each parabolic or U-shaped manifold 300 may comprise inner shell 10 and outer shell 20, with soft membrane layer 30 sandwiched in between the two shells. The components may be combined using various means, including, for example, but not limited to, being clipped together and/or be mounted together by short screws 50. Each U-shaped manifold may comprise an inlet to receive fluid into its hollow layer. The inlet may be positioned at approximately the vertex of the U-shaped 300.

The inner shell 10 may have cutouts or holes (hereinafter referred to as "holes") on each side. The holes may be enabled to provide for jets of fluid to exit the apparatus 100 and projected onto a user's teeth. The two U-shaped manifolds 300 may be connected together by a rotating inlet joint 200. The connection may provide for a symmetrical, approximately H-shaped manifold. The connection of the three components (two U-shaped manifolds and the rotating inlet joint) may be connected by various means, including, for example, but not limited to, being snapped together and/or attached by a longer screw 55.

In some embodiments, to prevent fluid leakage, an enhanced seal may be provided by using one or more O-rings 60 between the rotating inlet joint 200 and each outer shell 20. Alternately, the seal may be accomplished by precision molding, or other means without the use of O-rings 60. The fluid may enter through an inlet channel of the rotating inlet joint 200, and then channeled to each U-shaped manifold 300 through their corresponding inlet openings in the outer shell 20. The fluid may then travel between the outer shell 20 and the soft membrane layer 30, before being projected as a stream or a jet of fluid out of the outlet holes of each U-shaped manifold 300. In this way, a jet of fluid may be provided onto a user's teeth through the soft membrane layer 30 and/or holes in the inner shell 10.

Regarding the aforementioned rotating inlet joint 200, the rotating inlet joint 200 consistent with the present disclosure may interface with a variety of methods for delivering fluid, past the joint, into each manifold. These include, but are not limited to, fluid pumps, faucet or showerhead attachments, cordless handles, pressurized fluid containers, dental equipment, and other fluid delivery solutions.

The present disclosure describes two manifold components 300, a rotating inlet joint 200, the function, and low friction movement aspects of the apparatus 100. Each manifold component 300 may be designed in a U-shape with aligned fluid orifices over the buccal and lingual sides of teeth. Accordingly, the two manifolds 300 may be combined to cover both top and bottom teeth at the same time. The apparatus 100 may be designed with respect to ergonomics. Data from ergonomics research necessitated the design of the apparatus 100 as, for example, two U-shapes combined, single U-shape, H-shape, X-shape, a chromosome shape, or similar shapes.

The rotating inlet joint 200 may be constructed in a manner to provide consistent, alternating, and/or pulsing fluid flow into each manifold 300 while allowing rotation, via the rotating inlet joint about a vertical axis of symmetry for comfortable movement across teeth. A joint may serve as a handle attaching the manifolds to enable necessary rotation. There are multiple methods of accomplishing the rotation of the joint 200, each with their own practical/engineering considerations consistent with the present disclosure.

The function of the present disclosure includes the apparatus 100 being swept across the user's mouth from one rear molar to the other rear molar. FIG. 27 demonstrates apparatus 100 performing the sweeping motion. In some embodiments, rollers having a motive force applied via the inlet/handle and the tooth/gum line may guide the sweeping motion while the inlet joints rotates about the vertical axis.

The present disclosure provides advantages of the aforementioned manifolds 300 over conventional devices, including, but not limited to, for example:
- providing fast action when compared to single water jets, water picks, or water flossers, enabling the user to wash their mouth and floss more efficiently,
- providing an ability to be certain that the fluid is appropriately aimed to the appropriate portions of the user's teeth, as scientific literature shows that oral irrigation is most effective when delivered at a 90° angle, which is hard to maintain with a single fluid jet;
- providing ease of use when compared to a single fluid jets, water picks, and manual flossing, which may be especially important for children, elderly, and those with disabilities, for whom ease of use may be more of a medical necessity than a convenience;
- providing an ability to reclean specific sections of the user's teeth when compared to a mouthguard;
- providing an assurance that no spot is missed, no matter what how the user's teeth are structured; and
- providing low friction movement to allow for easy movement across the tooth/gum line and to minimize discomfort.

II. VARIOUS CONFIGURATIONS

Figure 2:
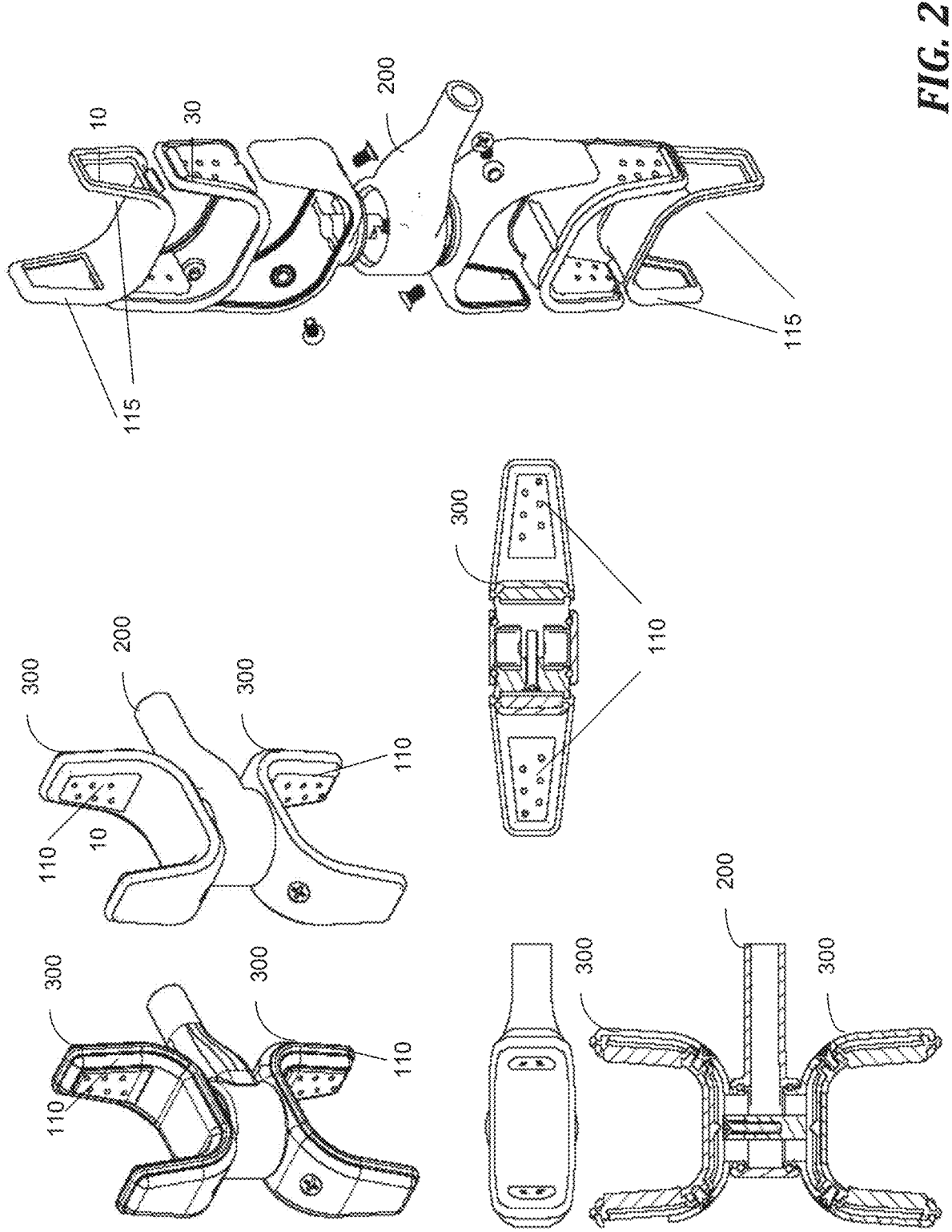
FIG. 2 illustrates an embodiment of the apparatus consistent with the present disclosure, that contains protruding pads on the membrane layer and uses no O-rings 60.

FIG. 2, illustrates an apparatus consistent with the present disclosure where the soft membrane 30 protrudes through the inner shell 10. The protrusion may take the form of a pad 110 coming out through a cutout opening 115 in the inner shell 10. The soft membrane pad 110 provides extra comfort for a user. The pad 110 may contain the holes for providing the fluid jets.

Figure 3:
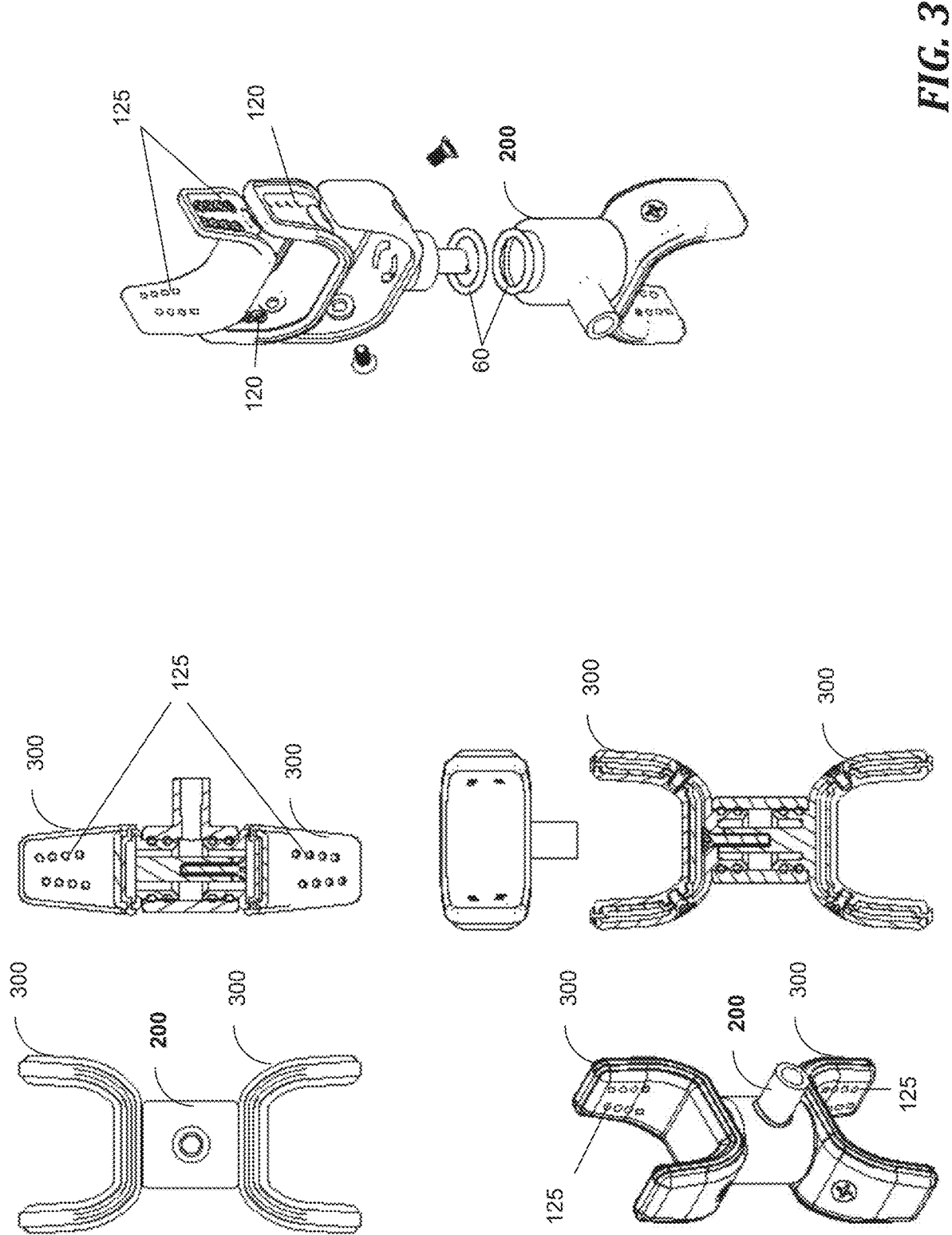
FIG. 3 illustrates an embodiment of the apparatus, consistent with the present disclosure, that contains non-protruding outlet holes on the inner shell and uses two sets of O-rings.

FIG. 3 illustrates an embodiment of the apparatus 100 with holes 125 on the inner shell 10. The inner shell holes 125 may align with the holes on the soft membrane layer 120 to provide fluid jets. As with any embodiment consistent with the present disclosure, the holes may vary in size, thereby changing the fluid pressure of the jet and/or changing the volume of fluid exerted on to teeth.

In embodiments of the apparatus 100 wherein a fluid pump is present, the fluid pressure at the entrance point at the inlet opening of the inlet joint 200 may be limited. The pressure may be limited such that the pressure from fluid jets is non-destructive to user's gums. Limiting the fluid pressure may prevent user injury.

Consistent with some embodiments of the present disclosure, as the fluid flows through the apparatus 100, the fluid pressure may drop. This represents a difference A between fluid pressure at the entrance point at the inlet opening of the inlet joint 200 and the fluid pressure as it exits the manifold 300 holes. In this way, the pressure loss inside of apparatus 100 may not exceed A. In some embodiments, the flow path inside the apparatus 100 may be small, for example on the order of tens of millimeters, which may minimize losses from straight sections. The remaining losses in pressure may be attributed primarily to one or more junctions, bends, constrictions, branches, and the like within the apparatus 100. Embodiments may include, but not be limited to, the following junctions:

1. Inlet junction—where fluid flow changes direction within the inlet joint 200, from the protruding inlet to the upper and lower manifolds 300.
2. First manifold junction—where fluid flow changes direction as it enters the manifold 300 from the inlet joint 200, and turns toward one side of the manifold 300, such as buccal or lingual side.
3. Second manifold junction—where fluid flow changes direction from traveling laterally to traveling upward through the manifold 300 towards the openings.

In some embodiments of the apparatus 100 consistent with the present disclosure, the aforementioned inlet junction of the inlet joint 200 may comprise a rectangular form for maximal use of space. The pressure losses may be calculated by:

$$\delta p = k \cdot 0.5 \cdot \rho \cdot v^2$$

Assuming the length of the aforementioned rectangular inlet junction is a and the width is b, the hydraulic diameter of the rectangular duct may be calculated with:

$$D_r = 2 \cdot ab/(a+b)$$

As minor loss coefficients may not exist for a rectangular to circular t-junction, the hydraulic diameter of the rectangular duct may be substituted as an approximation and the minor loss coefficient for the circular t-junction k=2 may be used. With a total flow rate of Q, the pressure loss through the aforementioned inlet junction may be given by $\delta p_1$ where $\delta p_1$ may be calculated by:

$$\delta p_1 = \rho \cdot \left( Q / (0.5 \pi D_r^2) \right)^2$$

In some embodiments consistent with the present disclosure, the inlet joint 200 may provide rotation around a manifold 300. The rotation may necessitate a circular form of the aforementioned first manifold junction. In some embodiments consistent with the present disclosure, the top and bottom manifolds may be joined by a retaining screw 55. In such embodiments, an opening for fluid passage in a form known to an ordinary artisan as an annulus may be formed between the retaining screw 55 and the rotating inlet joint 200. The hydraulic diameter of the annulus may be calculated by:

$$D_a = (D_{out}^2 - D_{in}^2)^{1/2}$$

As with the fluid pressure loss in the aforementioned inlet joint, the fluid pressure loss in the first manifold junction may be given by $\delta p_2$ where $\delta p_2$ may be calculated by:

$$\delta p_2 = \rho \cdot (Q/(0.5\pi D_a^2))^2$$

In some embodiments consistent with the present disclosure, the second manifold junction may comprise a smooth right angle turn. The fluid pressure loss in the second manifold junction in the form of a smooth right angle turn is given by $\delta p_3$ which may be calculated by:

$$\delta p3 = 0.9\rho \cdot (Q/(\pi D_h^2))^2$$

The sum of the fluid pressure losses may be represented as $\Delta$ where $\Delta$ may be calculated by:

$$\Delta = \delta p_1 + \delta p_2 + \delta p_3$$

The equations, in combination with space constraints that depend on the specific embodiment, set the minimum diameters. Given the measurements of the apparatus 100, maximum fluid pressure entering the apparatus 100 may be calculated or approximated using the aforementioned formulas. The maximum fluid pressure calculation may be used to further enhance the apparatus 100 by, for example, but not limited to, limiting fluid pressure provided by an external source to prevent damage to a user's gums.

Figure 4:
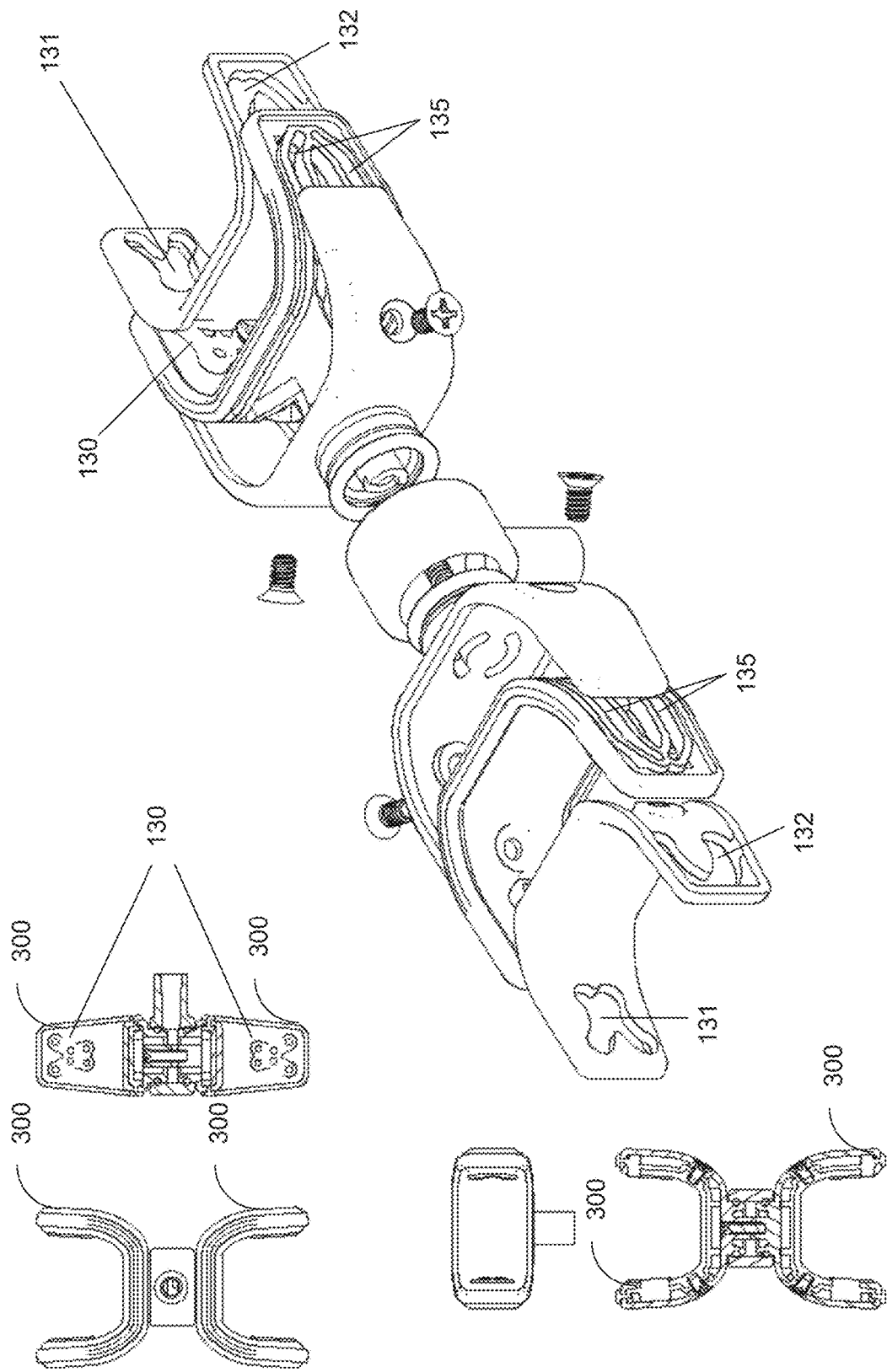
FIG. 4 illustrates an embodiment of the apparatus, consistent with the present disclosure, that contains protruding outlet holes on the membrane layer, uses one set of O-rings, and provides fluid flow channels on the membrane layer.

Consistent with various embodiments of the present disclosure, the apparatus 100 may contain soft protrusions surrounding the openings for jets 130, as illustrated in FIG. 4. The protrusions 130 may be part of the soft membrane 30 and designed to fit through a similarly shaped cutout in the inner shell 131. As FIG. 4 illustrates, the cutout on one side of the apparatus 131 may be of a different shape than the cutout on the second side of the apparatus 132. The aforementioned design may allow for fluid jets not to intersect, thereby cleaning teeth more effectively.

FIG. 4 also shows fluid channels 135 that may be designed within the soft membrane layer 30. The fluid channels 135 direct fluid to the openings from which the fluid may be projected onto teeth. The fluid channels 135 may provide fluid conservation, enhanced control over fluid pressure, and enhanced seals with the outer shell 20.

Figure 5:
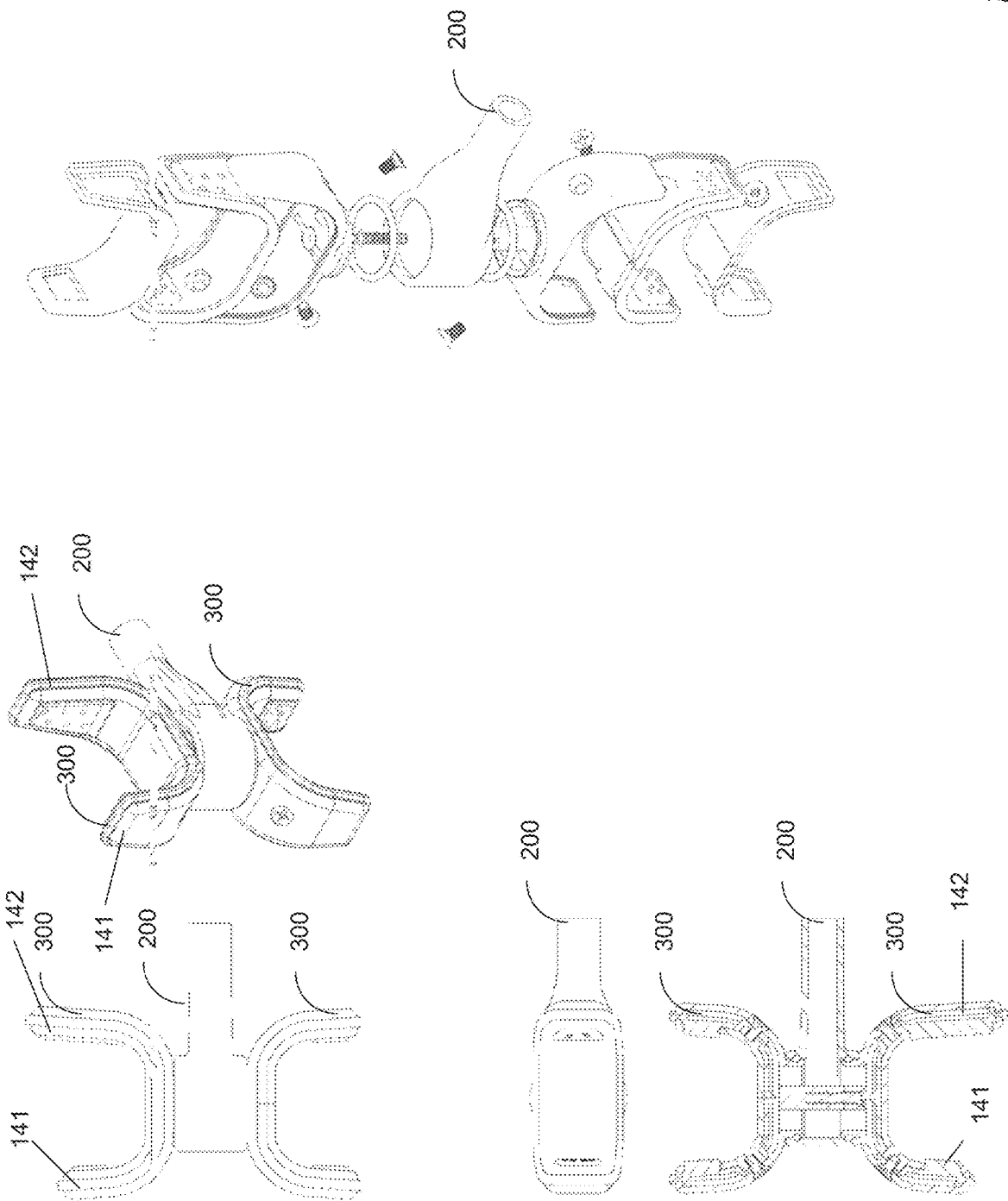
FIG. 5 illustrates an embodiment of the apparatus with different heights for the buccal and lingual sides that is consistent with the present disclosure.

In certain embodiments consistent with the present disclosure, each U-shaped manifold 300 may have sides with different heights, as illustrated in FIG. 5. The shorter side 141 may be designed to be located on the lingual side of the teeth, while the longer side 142 may be designed to be located on the buccal side. In some embodiments, the different height manifold may be present only on the top side of the apparatus 100, only on the bottom side of the apparatus 100, or both top and bottom sides of the apparatus 100. For some users, the different heights may provide enhanced alignment of the apparatus 100 in the mouth and enhanced cleaning of teeth by covering a larger area with fluid flow.

Figure 6:
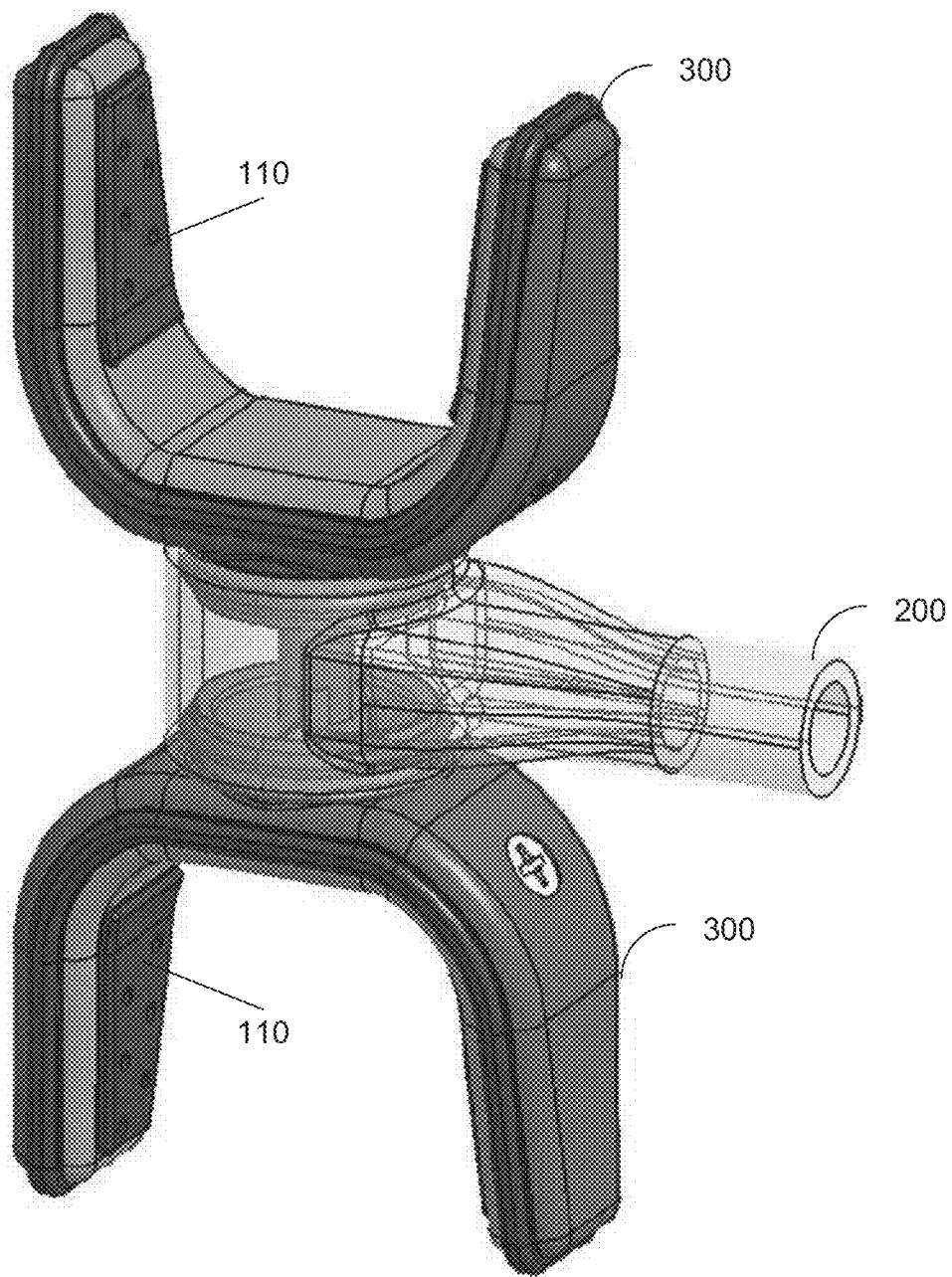
FIG. 6 illustrates an isometric view of the apparatus consistent with the present disclosure with protruding pads on the membrane layer and a translucent/transparent inlet joint.

FIG. 6 illustrates an embodiment of the apparatus 100 utilizing the aforementioned soft pads 110 and a rotating inlet joint 200 which may be transparent/translucent. The soft pads 110 may provide extra comfort, while the translucent joint 200 allows a user to see the fluid flow through the apparatus 100. The joint 200 may range from fully opaque to fully transparent. The joint 200 may be constructed of any color, while opaque or translucent. Even though FIG. 6 discloses a rotating inlet joint 200 that is transparent, it should be understood that any and all parts of the apparatus 100 consistent with the present disclosure may have varying degree of transparency, ranging from fully opaque to fully transparent.

Figure 7:
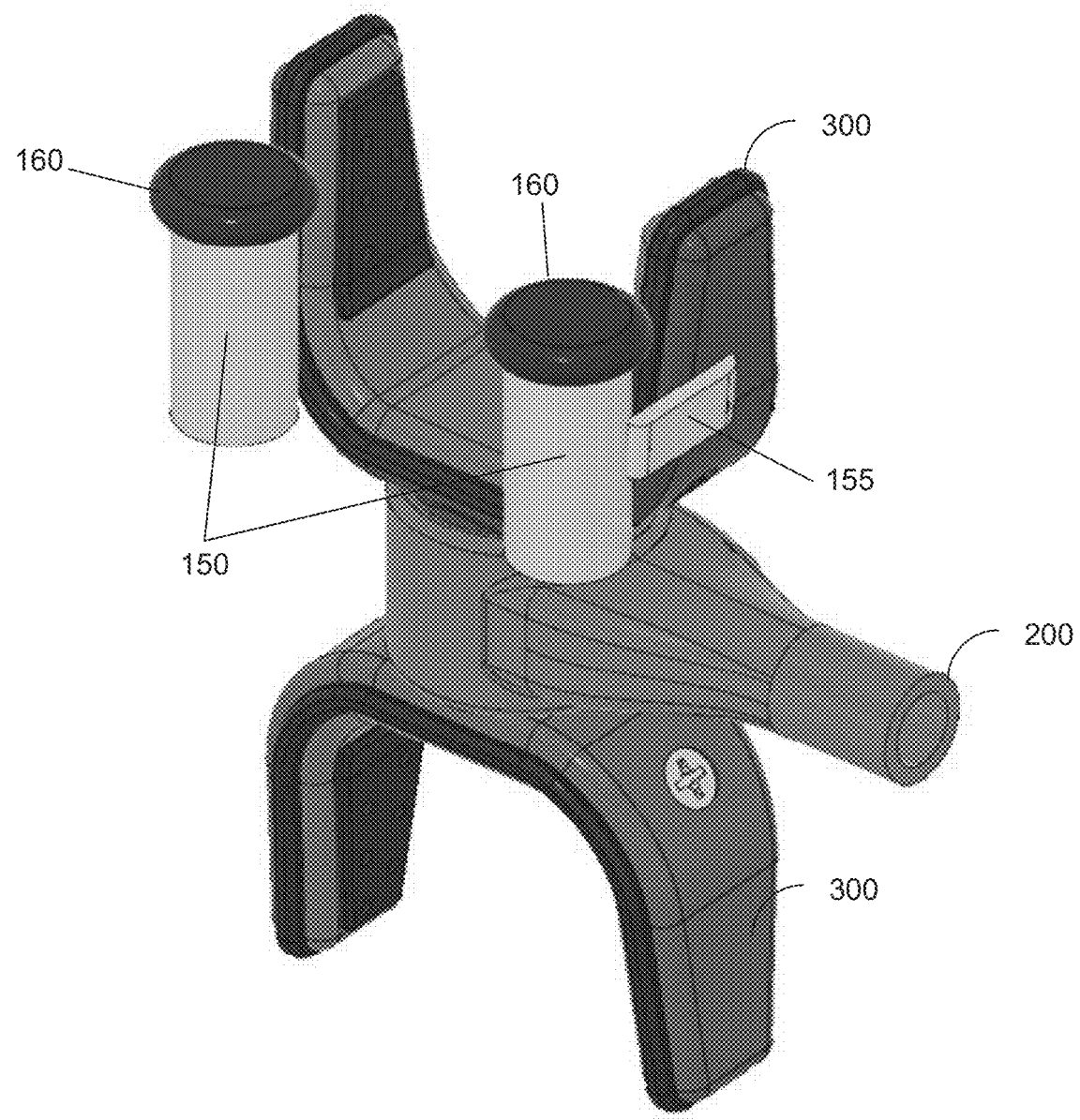
FIG. 7 illustrates an embodiment of the apparatus consistent with the present disclosure, with motors mounted on one side of the apparatus via sprung supports and soft wheels to drag the apparatus by applying force to the gumline.

FIG. 7 illustrates an embodiment utilizing small, soft wheels 160 as guides for smooth movement of the apparatus 100 consistent with the present disclosure. The wheels 160 may be mounted on top of small enclosures 150, containing motors, any device providing motive force, or any regulator of rotational resistance. The motor enclosures 150 may be attached to the apparatus 100 via sprung supports 155. The sprung supports may be designed to provide slight back and forth movement of the motor enclosures 150 with slight resistance, providing better comfort and fitment for a larger group of users. The motion control mechanism comprising soft wheels 160, motors inside motor enclosures 150 and sprung supports 155 may provide smooth movement of the apparatus by applying pressure along the gum line through the soft wheels 160. The motion control mechanism may be mounted on the top manifold 300, bottom manifold 300, or both manifolds 300. Alternately, the wheels 160 may be attached to both top and bottom ends of the motor enclosure 150, thereby gliding along both top and bottom gun lines. The motors may be controlled with a computing device 900 consistent with the present disclosure. Alternately, the motors may be always activated during the powered-on state of the apparatus 100 consistent with the present disclosure. The motion control mechanism consistent with the present disclosure may be used to regulate the speed of the apparatus 100 sweeping motion within the user's mouth, providing optimal cleaning and preventing missed/under-cleaned areas.

In some embodiments of the apparatus 100, the aforementioned motion control mechanism may be used to massage the gums. The massaging of gums may be accomplished by gliding the apparatus 100 back and forth along the gumline. The wheels 160 may be comprised of a material for optimum gum massage. In some embodiments consistent with the present disclosure, a vibration device may be mounted inside or near the motion control mechanism, causing the wheels 160 to vibrate and enhance the massage of the gun line.

Furthermore, in some embodiments of the apparatus 100, the foregoing motion control mechanism may be used to remove plaque by gliding the apparatus along the teeth. The wheels 160 may be comprised of a material for optimum plaque removal. The aforementioned vibrating device may be employed to further enhance the removal of plaque. The plaque removal may be combined with the aforementioned gum massage in the apparatus 100 consistent with the present disclosure.

Figure 8:
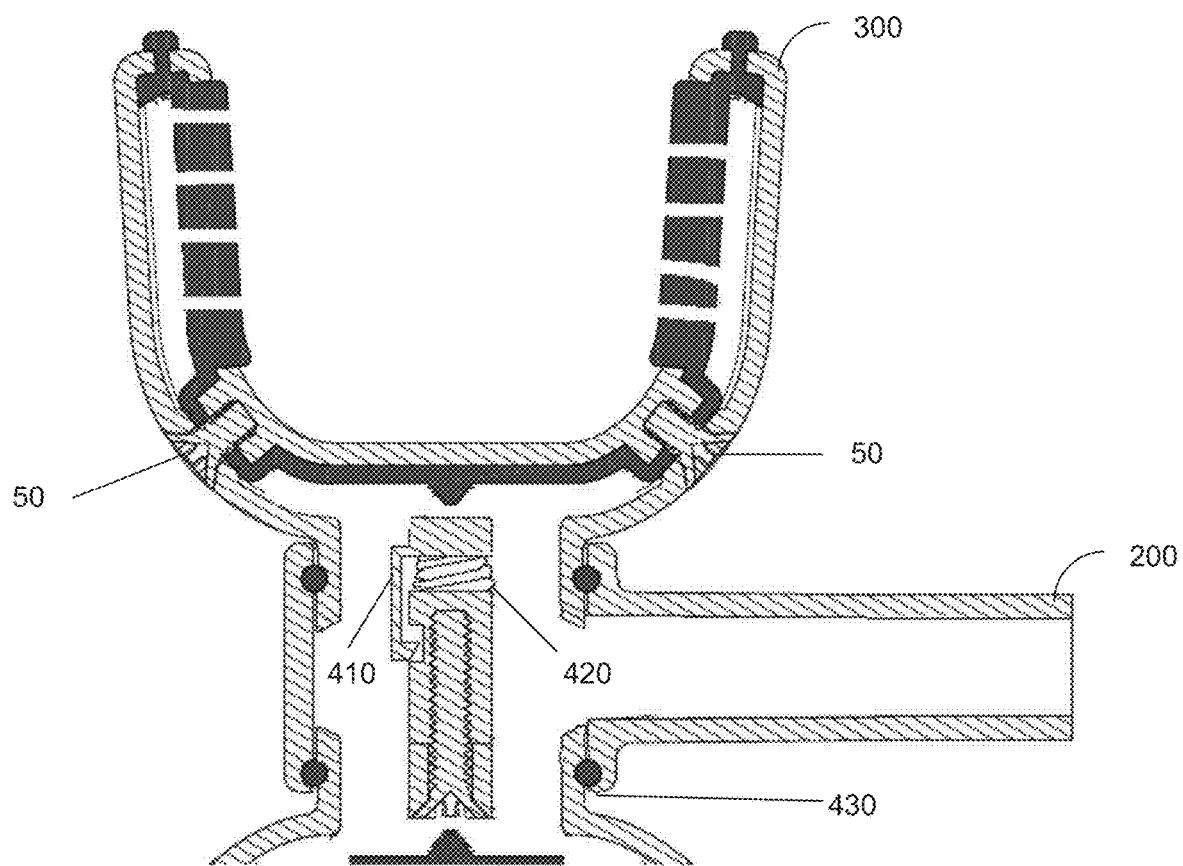
FIG. 8 illustrates a cutaway view of the apparatus consistent with various embodiments of the present disclosure, with an internal spring that allows motion between upper and lower parts of the apparatus, therefore providing height adjustment for fluid jet alignment and enhanced comfort.

FIG. 8 illustrates a cutaway of an apparatus 100 with a height adjustment mechanism. The mechanism comprises a joint 200 which allows for travel of a manifold 300 via extra space 430, a spring 420, and a hard-stop mechanism 410 that prevents over extension. The spring 420 may decompress with fluid pressure, and recompress when a user applies force to the manifolds 300 with the user's teeth. The height adjustment mechanism may provide some flexibility in the height of the device, providing for better fluid jet alignment. The height adjustment mechanism may also provide extra comfort due to semi free-floating of the manifolds 300. The height adjustment mechanism may adjust height based on pressure applied to the manifolds 300 by the user's teeth. Better cleaning may be achieved by providing enhanced alignment of fluid jets with teeth. The mechanism may be activated by applying pressure to the manifolds 300 via the user's teeth. In some embodiments consistent with the present disclosure, the activation of the apparatus 100 may happen upon applying pressure to the aforementioned height adjustment mechanism. The activation may comprise, but not limited to, starting the flow of fluid, enabling the aforementioned motion control mechanism, and other features disclosed herein.

In some embodiments, the aforementioned height adjustment mechanism may act as a joint, joining the upper and lower manifolds 300. In such embodiments, the rotating inlet joint 200 may be replaced with an alternate inlet mechanism.

The apparatus 100 consistent with some embodiments of the present disclosure may embody an anti-rotate mechanism, as illustrated in FIG. 9. The mechanism may comprise an extrusion with a tip comprising of an uneven surface 440 on one manifold 300 and a socket 445 on the second manifold 300, that accepts the tip 440 on the first manifold 300, with a surface designed to match the tip 440. By providing an uneven surface on the tip 440 and matching it on the socket 445, the apparatus 100 prevents misalignment of the manifolds 300 and unwanted rotation.

FIG. 9 also illustrates openings for fluid 450 on the bottom of a manifold 300 consistent with the present disclosure. The openings 450 comprise cutaways in at approximately the center of the outer shell 20. The openings 450 allow the fluid to flow into the manifold 300 to be projected onto teeth.

An apparatus 100 consistent with the present disclosure may alter the flow of fluid out of the openings forming jets. The flow of fluid may be altered for enhanced cleaning in multiple ways, such as, but not limited to:
  Pulsing—Where each jet may be activated for a short period of time, followed by a deactivation for a short period of time, then repeat of the cycle. Jets may be pulsed all together, independently, or in alternating manner.
  Alternating flow—Where activation of jets may be alternated between buccal and lingual sides and/or top and bottom manifolds 300.

Figure 10:
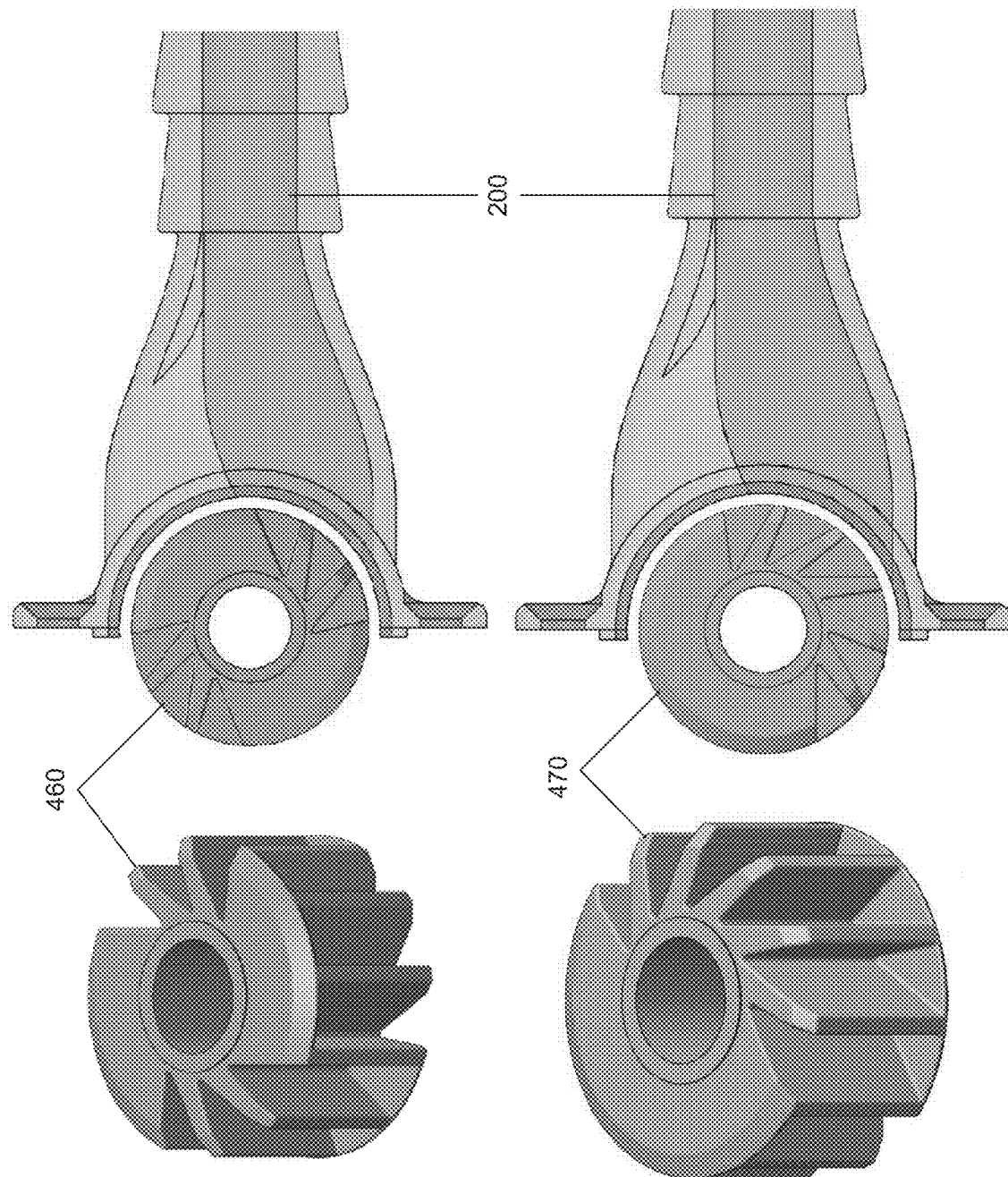
FIG. 10 illustrates two embodiments of a rotator wheel that directs alternating fluid flow for the apparatus consistent with various embodiments of the present disclosure.
Figure 12:
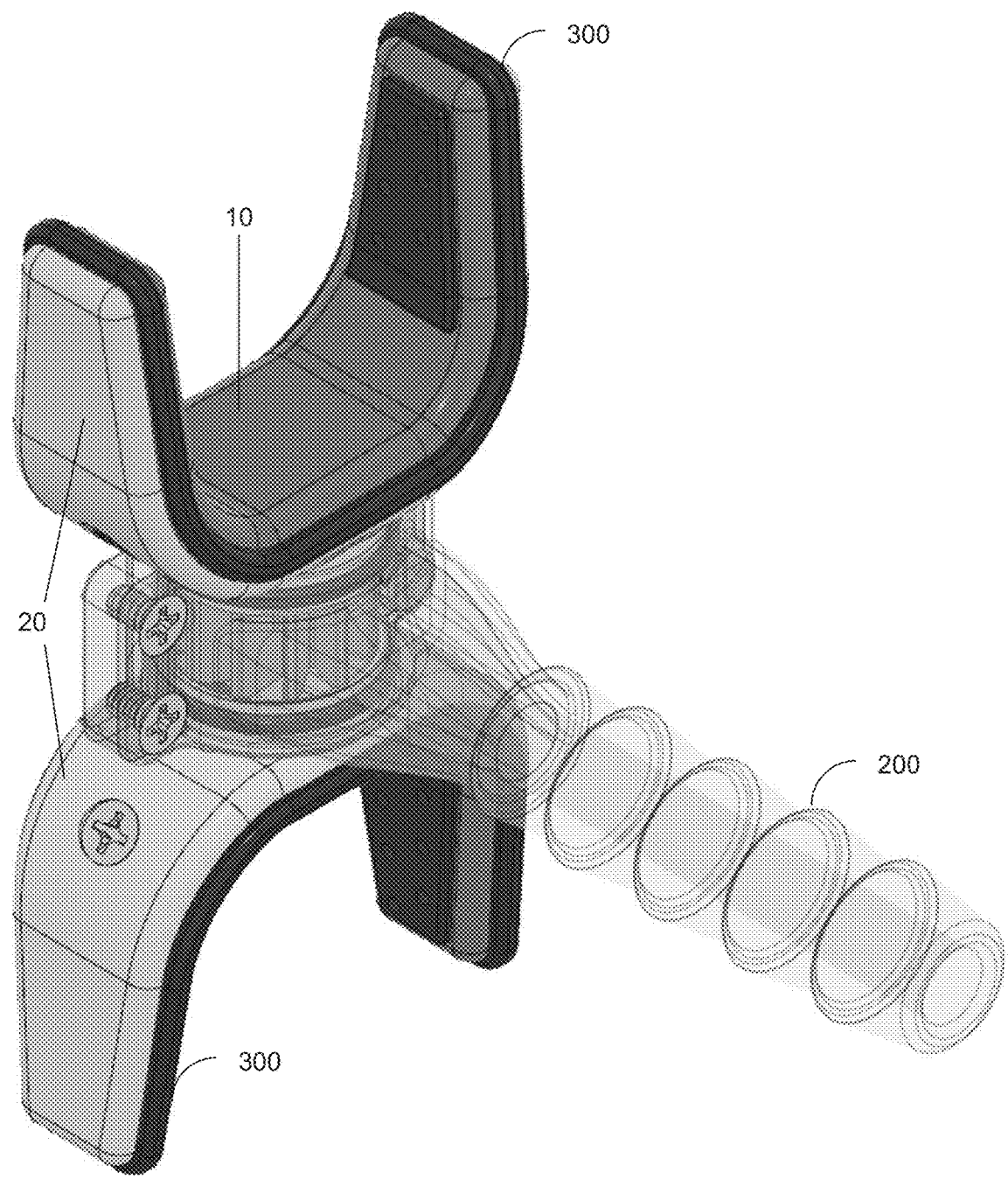
FIG. 12 illustrates an embodiment of the apparatus with a rotator wheel and translucent/transparent rotating inlet joint.
Figure 13:
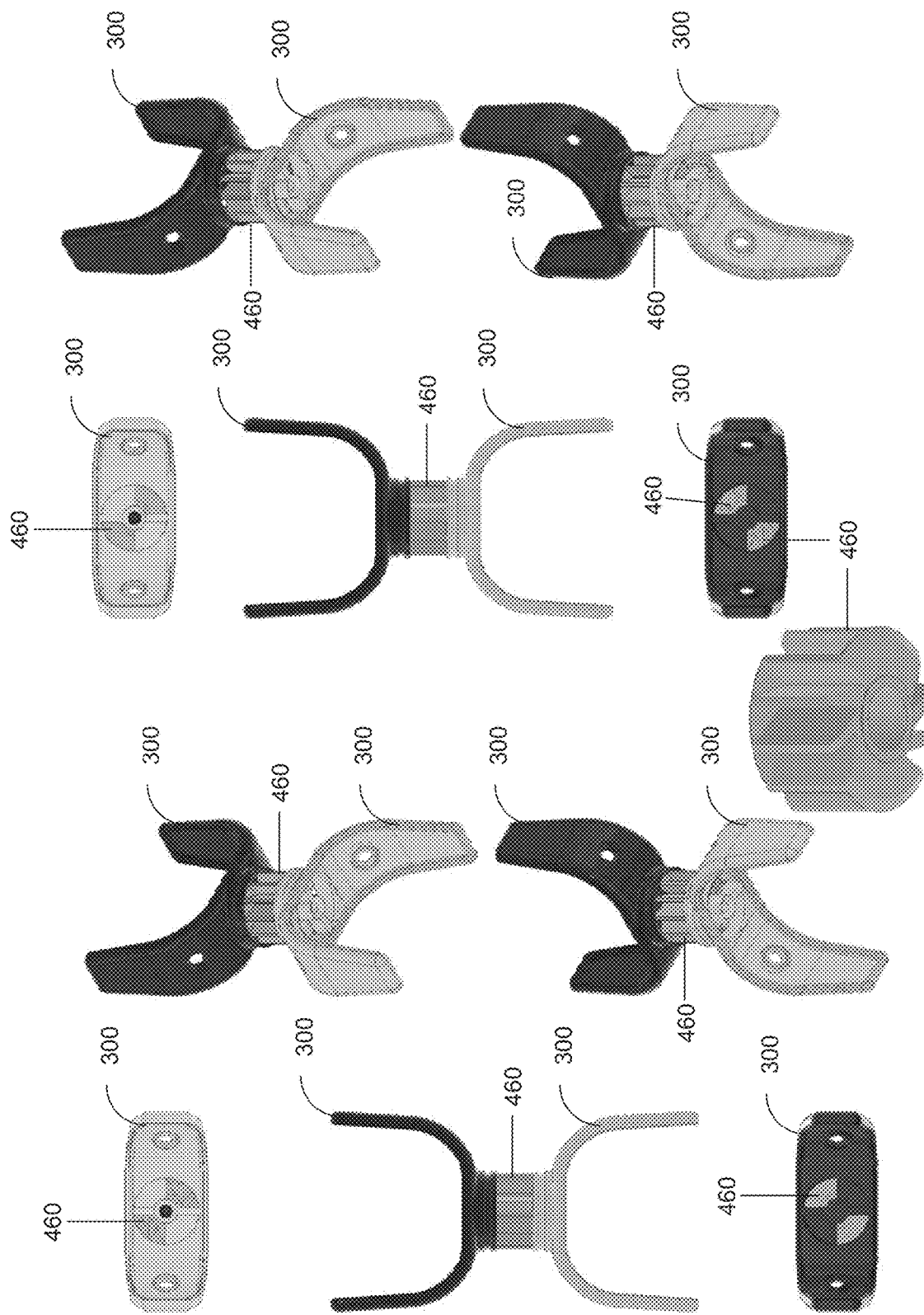
FIG. 13 illustrates an embodiment of the apparatus with the rotator wheel, where the fluid flow alternates between lower and upper teeth.

Consistent with the various embodiments of the present disclosure, the top/bottom alternation may be accomplished by a revolver part 460 mounted inside the rotating inlet joint 200, as illustrated by the examples provided in FIG. 10, FIG. 12 and FIG. 13. Although embodiments herein a described with respect to a revolving characteristic of the flow control and distribution means, other implementations may be used to achieve flow control and distribution.

The revolver part 460 may be designed as, for example, a blower wheel, wherein the revolver part 460 has fins extending outward from the center, that may allow it to spin from fluid flowing past/through it. The rotating inlet joint 200 may comprise an offset wall to divert fluid flow, spinning the revolver 460 in the desired direction. The revolver part 460 may have upper and lower walls at each quarter of the revolver 460. In some embodiments, every 50% may be blocked off in an alternated fashion on the top and bottom sides, projecting fluid in different directions, such as up or down. For example, first quarter may have the top blocked off, pushing fluid down, second quarter may have the bottom blocked off, pushing fluid up, third quarter may have the top blocked off, pushing fluid down, and fourth quarter may have the bottom blocked off, pushing fluid up.

Figure 11:
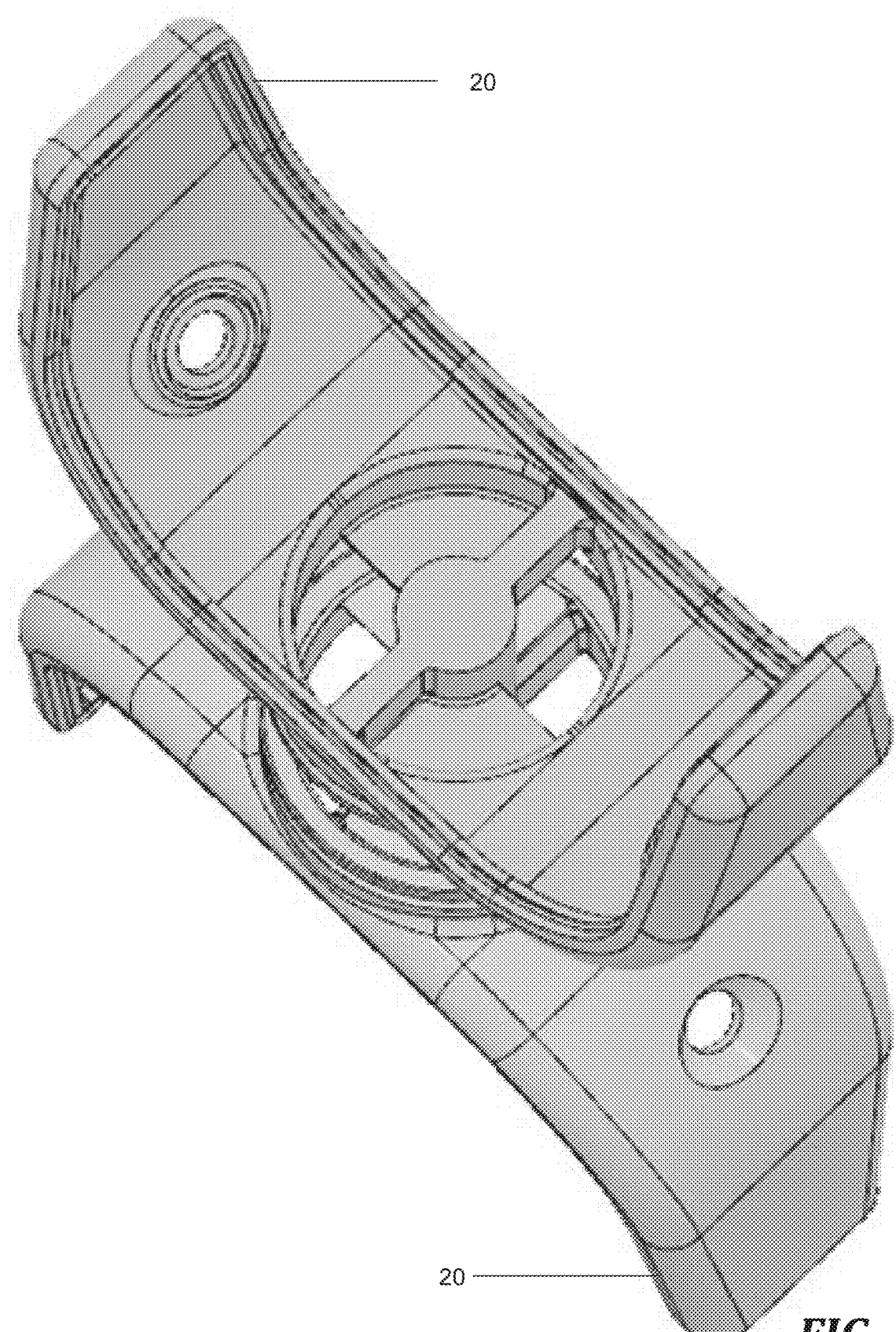
FIG. 11 illustrates the outer shell of the top manifold, and the outer shell for the bottom manifold, consistent with the present disclosure, wherein the openings for fluid flow on both outer shells line up.

In some embodiments, the outer shells 20 of the manifolds 300 may have two cutouts for fluid flow corresponding to the wheel 460 quarters positioned diagonally opposing each other, such that if you take two identical outer shells 20 and flip one on top of the other in a reflective manner, the quarters line up, as illustrated in FIG. 11. In this way, the revolver 460 will only push fluid into one manifold 300 at a time. As the revolver 460 spins, its top openings may line up with the openings on the top manifold 300, providing an upward flow of fluid, while the bottom openings may line up with the walls on the bottom manifold 300, blocking the downward flow of fluid. As the fluid continues to flow, the revolver 460 may continue to spin, which in turn may allow its top openings to line up with the walls on the top manifold 300, blocking an upward flow of fluid, while the bottom openings may line up with the openings on the bottom manifold 300, providing the downward flow of fluid. Different fluid pressure may be provided in order to alter the rate of revolver 460 spinning, thereby altering how often the flow switches from top to bottom manifold 300, and vice versa.

Figure 14:
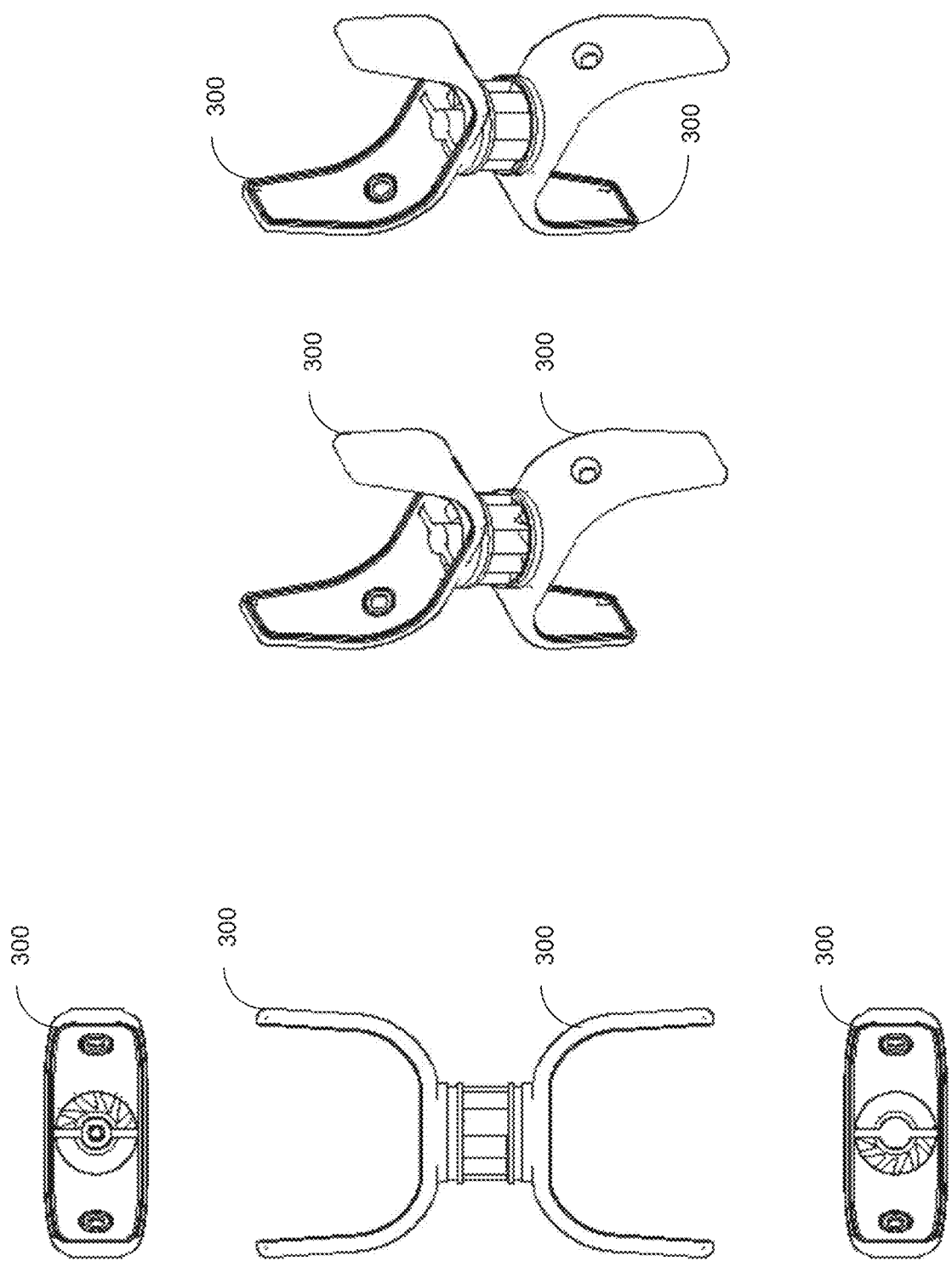
FIG. 14 illustrates an embodiment of the apparatus with the rotator wheel where the fluid flow alternates between buccal and lingual sides of teeth.

Still consistent with embodiments of the present disclosure, the buccal/lingual alternation may be accomplished by a revolver part 470 mounted inside the rotating inlet joint 200, as illustrated by the examples provided in FIG. 10, FIG. 12 and FIG. 14. The revolver part 470 may be designed as, for example, a blower wheel, wherein the revolver part 470 has fins extending outward from the center, that may allow it to spin from fluid flowing past/through it. The rotating inlet joint 200 may comprise an offset wall to divert fluid flow, spinning the revolver 470 in the desired direction. The revolver part 470 may have upper and lower walls each half of the revolver 470, wherein every 50% is blocked off in an alternated fashion on the top and bottom sides, projecting fluid in different directions, such as up or down. For example, first half has the top blocked off, pushing fluid in one direction, second half has the bottom blocked off, pushing fluid in another direction, whereby one manifold will receive the fluid only on the buccal side, and the second manifold will only receive fluid on the lingual side. Different fluid pressure may be provided in order to alter the rate of revolver 470 spinning, thereby altering how often the flow switches from buccal to lingual side of the manifold 300, and vice versa.

In some embodiments, the manifolds 300 may have two cutouts for fluid flow corresponding to the revolver 470 halves positioned opposing each other, such that each opening may provide the flow of fluid to the corresponding side, buccal or lingual, of the manifold only. In this way, the revolver 470 may only push fluid into one side of a manifold 300 at a time. As the revolver 470 spins, its openings may line up with one opening on the top manifold 300 and another opening on the bottom manifold 300, providing an upward and downward flow of fluid to the corresponding buccal/lingual side of each manifold 300. As the fluid continues to flow, the revolver 470 may continue to spin, which in turn may allow its top openings to line up with the openings on the opposite side of each manifold 300, switching the flow from buccal to lingual side on each manifold 300, and vice versa. Different fluid pressure may be provided in order to alter the rate of revolver 470 spinning, thereby altering how often the flow switches from top to bottom manifold 300, and vice versa. In some embodiments consistent with the present disclosure, alteration of the flow may be binary or sinusoidal.

In various embodiments, the flow of the fluid may be altered based on position of the apparatus 100 within a mouth and/or speed with which the apparatus 100 glides within a mouth. Here, the apparatus 100 may comprise one or more sensing devices (e.g., as further disclosed with reference to computing device 900) that senses the location of the rotating inlet joint 200. A computing device 900 consistent with the present disclosure may monitor the sensor, and therefore monitor the current angle of the rotating inlet joint 200 relative to the manifolds 300, and calculate the rate of change of the angle.

Figure 15:
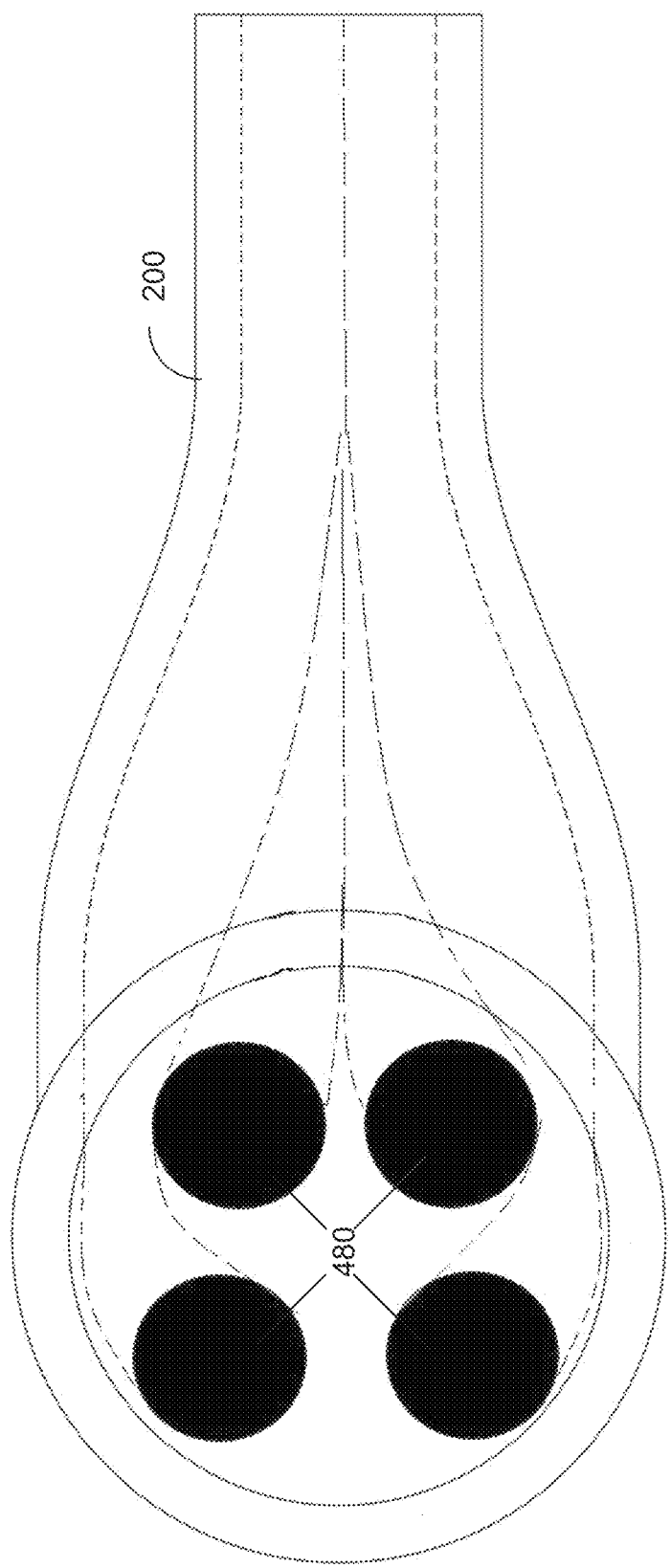
FIG. 15 illustrates an embodiment of the rotating inlet joint designed with four individual fluid channels.

As an example, based on the current angle of the rotating inlet joint 200, the computing device 900 may derive the current location within a mouth. Based on the calculated rate of change of the angle, the computing device 900 may derive the speed of gliding within a mouth. The rotating inlet joint 200 may be designed with four channels of fluid flow 480, as illustrated by the examples provided in FIG. 15.

Figure 16:
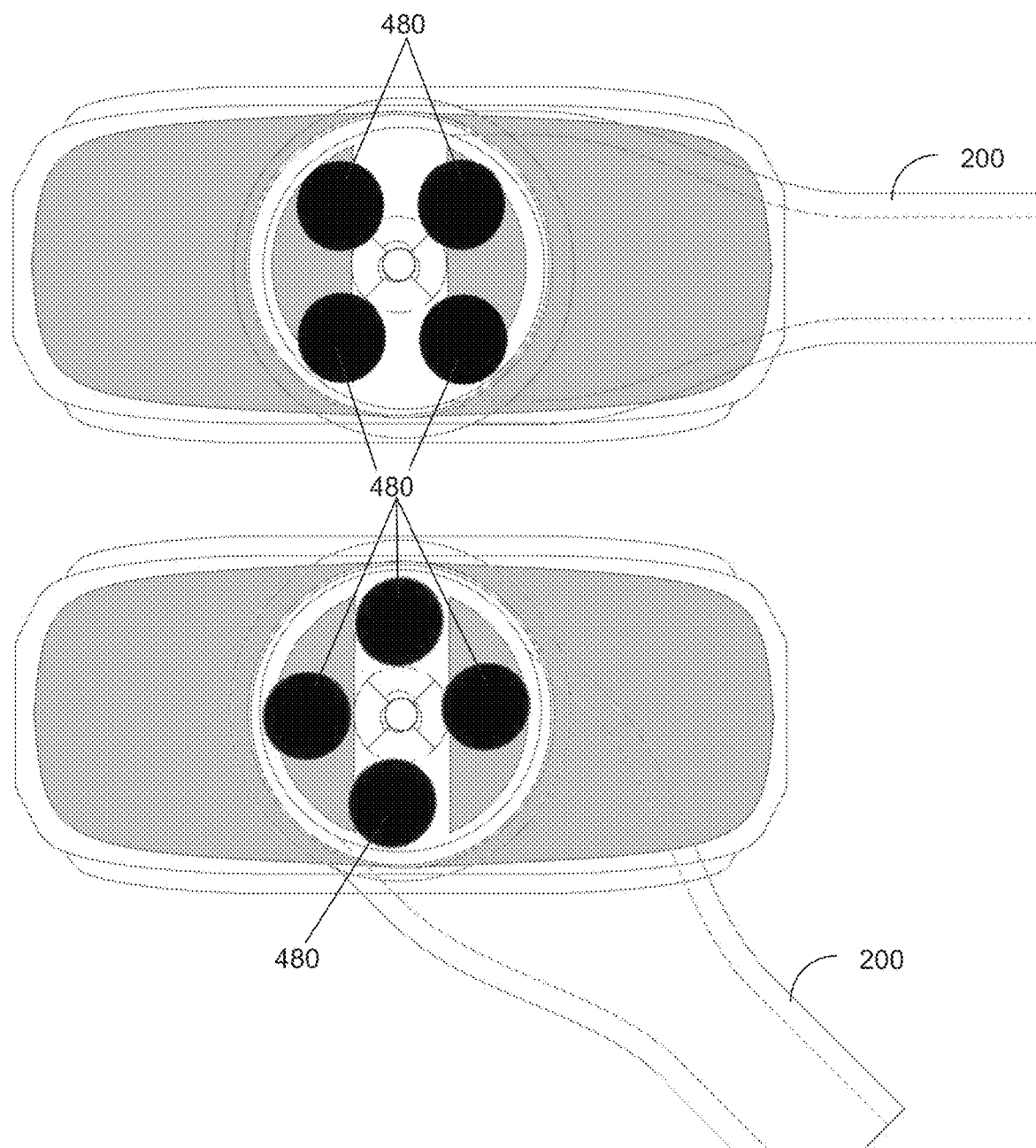
FIG. 16 illustrates different positions of the rotating inlet joint and how the rotation alters fluid flow within the apparatus consistent with various embodiments of the present disclosure.
Figure 17:
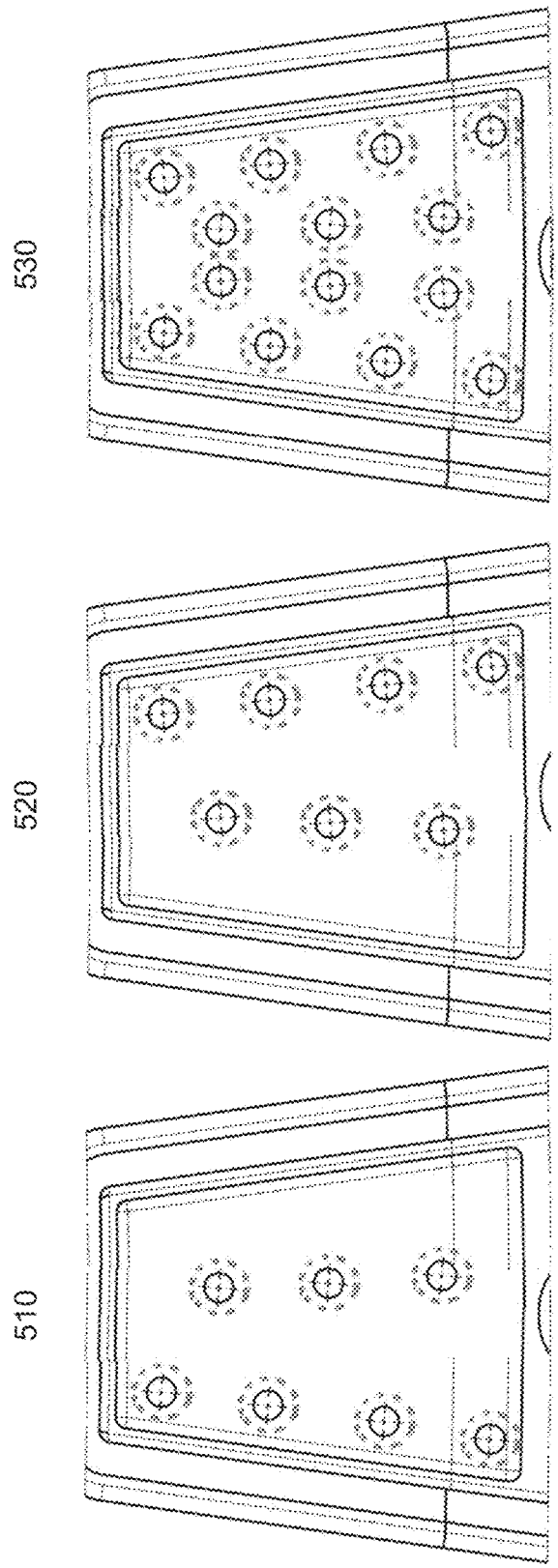
FIG. 17 illustrates one example of non-intersecting fluid jet positions for the apparatus consistent with various embodiments of the present disclosure.

FIG. 16 illustrates how different angles of the rotating inlet joint 200 may allow the fluid to flow from different channels into different manifolds 300 and/or different sides of the manifold. The computing device 900 may notify the user of the speed and location of the apparatus 100. By controlling which channel the fluid flows through at any given time, the computing device 900 may alter the fluid flow in numerous ways, such as, but not limited to:

Alternating flow from buccal to lingual based on location and/or speed;
Alternating from top to bottom based on location and/or speed;
Pulse based on location and/or speed;
Pulse and alternate flow based on location and/or speed;
Change fluid pressure based on location and/or speed;
Change fluid pressure and pulse based on location and/or speed;
Change fluid pressure and alternate flow based on location and/or speed; and
Change fluid pressure, pulse and alternate flow based on location and/or speed.

The aforementioned fluid flow control methods may be used individually, or in combination with each other. Furthermore, an apparatus consistent with the present disclosure may control each jet individually, with or without a computing device 900.

FIGS. 17, 18, 19, 20, 21, 22, 23, 24, 25 and 26 illustrate different embodiments of hole layouts for providing jets of fluid expelled out an apparatus 100. 510 illustrates a layout on one side of the manifold 300, while 520 illustrates a layout on the second side of the manifold 300. Each side could be used on either the buccal or lingual side of the manifold. 530 illustrates a superposition of the orifices, wherein the first side layout 510 is superimposed on the second side layout 520. In some embodiments, each of the two sides can have similar layouts. In other embodiments, the layouts can be staggered, or asymmetrical, such that the jets of fluid being expelled from one side 510 do not line up with the jets of fluid being expelled from the second side 520. Staggered layout may be preferred, as it provides improved cleaning compared to a layout where jets line up. Furthermore, staggered layout may provide increased safety by reducing the pressure exerted onto user's gums.

FIG. 27 illustrates an apparatus 100 consistent with the present disclosure within a human jaw. While the jaw is that of a 50th percentile human male for illustrative purposes, it should be understood the apparatus may be used to clean teeth of any mammal, or any object vaguely resembling the shape of teeth that could be cleaned in a sweeping manner.

Certain embodiments of the apparatus 100 consistent with the present disclosure may contain additional features, such as, but not limited to:

Toothbrush bristles may be mounted on the interior surfaces of the inner shell 100. The toothbrush bristles may allow to brush teeth while flossing for an enhanced cleaning.

UV and or IR illumination paired with a camera or an optical sensor to detect plaque and alert the user. The aforementioned devices and alerts may be controlled by a computing device 900 consistent with the present disclosure, which may also record the data to any medium compatible with the computing device 900 or the cloud. Furthermore, the recordings may automatically be uploaded to the platform operated by a dental practice or a medical entity.

Camera to record the gumline for future review, historical data, for a dentist, or for a study conducted by a third party. The camera may be controlled by a computing device 900, which may also save the recordings to any medium compatible with the computing device 900 or the cloud. Furthermore, the recordings may automatically be uploaded to the platform operated by a dental practice or a medical entity, platform of user's choice, or a third party conducting a study.

UV cleaning illumination, by use of ultraviolet germicidal irradiation or other methods. UV cleaning may reduce bacteria within a mouth. UV cleaning may be provided via use of UV light emitting diodes (LEDs) projected inside a mouth. UV cleaning may be used to clean the disclosed apparatus. In some embodiments consistent with the present disclosure, the cleaning may be performed by a different wavelength of the electromagnetic spectrum, such as, but not limited to, infrared or x-ray.

Plaque removing device, such as an aforementioned motion control mechanism or another mechanism. The disclosed mechanism may reduce and/or remove plaque with or without a computing device 900.

As may be apparent to a person having ordinary skill in the art, the features described herein may be combined with each other, creating numerous embodiments of the apparatus 100 consistent with the present disclosure. For example, an apparatus 100 consistent with the present disclosure may comprise soft pads protruding from the inner shell 10, fluid channels 135 embedded in the soft membrane 30, different height manifolds 300, tinted translucent rotating inlet joint 200 with, for example, multiple fluid channels (e.g., four), motion control mechanism with vibration, spring height adjustment, anti-rotate mechanism, alternating and pulsating jets based on speed and location of the apparatus 100 within a mouth, orifice patterns that do not intersect, toothbrush bristles, UV cleaning, gum massaging, cameras for gum recording and plaque detection, and be controlled by a computing device 900.

Consistent with the present disclosure, the joints and various components may be used with any of the proposed shapes of the apparatus 100 including the shapes depicted in the figures. Embodiments of the present disclosure, for example, are described above with reference to diagrams and/or operational illustrations of methods, systems, and apparatuses according to embodiments of the disclosure. The functions/acts noted in the U-shaped manifold 300 and/or components may occur out of the order as shown in any figure. For example, two U-shaped manifolds 300 shown in succession may in fact be executed substantially concurrently or the U-shaped manifolds 300 may sometimes be executed in the reverse order, depending upon the functionality/acts involved.

While certain embodiments of the disclosure have been described, other embodiments may exist. For example, an embodiment may exist wherein a suction tube is attached to the handle such that the tube sucks up the fluid in a user's mouth, avoiding a potential mess and providing extra comfort. The suction tube may also be built within the apparatus 100 consistent with the present disclosure. Additionally, another embodiment consistent with the present disclosure uses a X-shaped head. The X-shaped head may be configured to have a V-shape for the upper teeth and the lower teeth together. In another embodiment, a U-shaped or a V-shaped manifold head may be configured to function on either the upper teeth or lower teeth at one time. The manifold head may be alternatively used for the upper teeth or lower teeth for the entire mouth of a user. In the embodiments, the U-shape manifold 300 may be rounded or square at the corners for the best fit in a user's mouth. Yet another embodiment consistent with the present disclosure may comprise an H-shaped apparatus that cleans both upper and lower teeth at the same time. While certain embodiments of the disclosure have been described, other embodiments may exist.

III. INTEGRATED AND EXTERNAL COMPUTING DEVICES

The apparatus 100 consistent with the present disclosure may be controlled by a computing device 900. The computing device 900 may comprise, but not be limited to; an embedded microcontroller within the apparatus, or a mobile computing device, or a microcomputer embedded in the pump system, or a remote computing device that communicates via various methods understood by a person having ordinary skill in the art.

Embodiments of the present disclosure may comprise a system having a central processing unit (CPU) 920, a bus 930, a memory unit 940, a power supply unit (PSU) 950, and one or more Input/Output (I/O) units. The CPU 920 coupled to the memory unit 940 and the plurality of I/O units 960 via the bus 930, all of which are powered by the PSU 950. It should be understood that, in some embodiments, each disclosed unit may actually be a plurality of such units for the purposes of redundancy, high availability, and/or performance.

Figure 28:
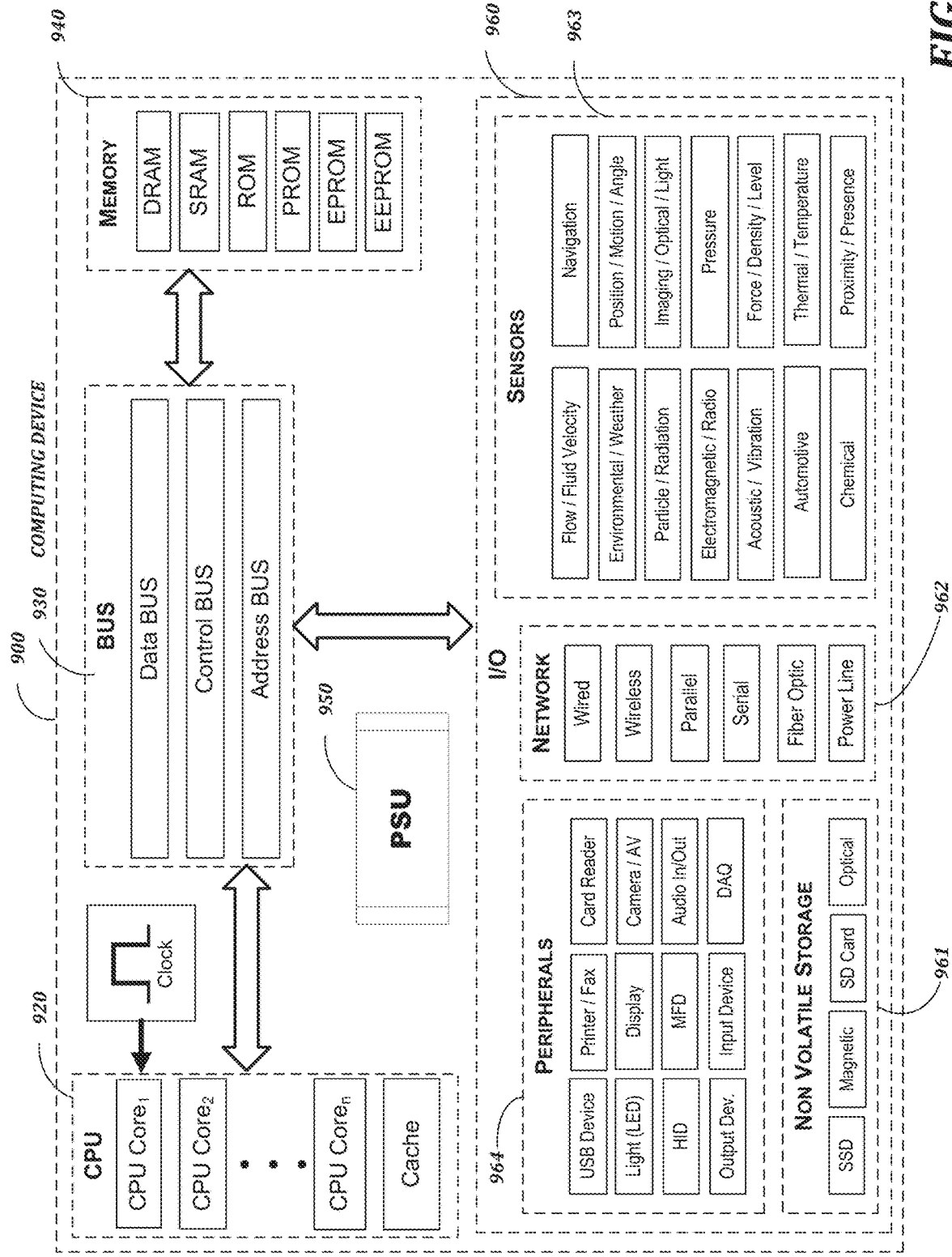
FIG. 28 illustrates a block diagram of a system including a computing device compatible with the various embodiments of the present disclosure.

FIG. 28 is a block diagram of a system including computing device 900. Consistent with an embodiment of the disclosure, the aforementioned CPU 920, the bus 930, the memory unit 940, a PSU 950, and the plurality of I/O units 960 may be implemented in a computing device, such as computing device 900 of FIG. 28. Any suitable combination of hardware, software, or firmware may be used to implement the aforementioned units. For example, the CPU 920, the bus 930, and the memory unit 940 may be implemented with computing device 900 or any of other computing devices 900, in combination with computing device 900. The aforementioned system, device, and components are examples and other systems, devices, and components may comprise the aforementioned CPU 920, the bus 930, the memory unit 940, consistent with embodiments of the disclosure.

Consistent with the embodiments of the present disclosure, the aforementioned computing device 900 may employ a communication system that transfers data between components inside the aforementioned computing device 900, and/or the plurality of computing devices 900. The aforementioned communication system will be known to a person having ordinary skill in the art as a bus 930. The bus 930 may embody internal and/or external plurality of hardware and software components, for example, but not limited to a wire, optical fiber, communication protocols, and any physical arrangement that provides the same logical function as a parallel electrical bus. The bus 930 may comprise at least one of, but not limited to a parallel bus, wherein the parallel bus carry data words in parallel on multiple wires, and a serial bus, wherein the serial bus carry data in bit-serial form.

Consistent with the embodiments of the present disclosure, the aforementioned computing device 900 may employ hardware integrated circuits that store information for immediate use in the computing device 900, known to the person having ordinary skill in the art as primary storage or memory 940.

Consistent with the embodiments of the present disclosure, the aforementioned computing device 900 may employ the communication system between an information processing system, such as the computing device 900, and the outside world, for example, but not limited to, human, environment, and another computing device 900. The aforementioned communication system will be known to a person having ordinary skill in the art as I/O 960. The I/O module 960 regulates a plurality of inputs and outputs with regard to the computing device 900, wherein the inputs are a plurality of signals and data received by the computing device 900, and the outputs are the plurality of signals and data sent from the computing device 900. The I/O module 960 interfaces a plurality of hardware, such as, but not limited to, non-volatile storage 961, communication devices 962, sensors 963, and peripherals 964. The plurality of hardware is used by the at least one of, but not limited to, human, environment, and another computing device 900 to communicate with the present computing device 900. The I/O module 960 may comprise a plurality of forms, for example, but not limited to channel I/O, port-mapped I/O, asynchronous I/O, and Direct Memory Access (DMA).

Consistent with the embodiments of the present disclosure, the aforementioned computing device 900 may employ the non-volatile storage sub-module 961, which may be referred to by a person having ordinary skill in the art as one of secondary storage, external memory, tertiary storage, off-line storage, and auxiliary storage. The non-volatile storage sub-module 961 may not be accessed directly by the CPU 920 without using intermediate area in the memory 940. The non-volatile storage sub-module 961 does not lose data when power is removed and may be two orders of magnitude less costly than storage used in memory module, at the expense of speed and latency.

Consistent with the embodiments of the present disclosure, the aforementioned computing device 900 may employ the communication sub-module 962 as a subset of the I/O 960, which may be referred to by a person having ordinary skill in the art as at least one of, but not limited to, computer network, data network, and network. The network allows computing devices 900 to exchange data using connections, which may be known to a person having ordinary skill in the art as data links, between network nodes. The nodes comprise network computer devices 900 that originate, route, and terminate data. The nodes are identified by network addresses and can include a plurality of hosts consistent with the embodiments of a computing device 900. The aforementioned embodiments include, but not limited to personal computers, phones, servers, drones, and networking devices such as, but not limited to, hubs, switches, routers, modems, and firewalls.

Consistent with the embodiments of the present disclosure, the aforementioned computing device 900 may employ the sensors sub-module 963 as a subset of the I/O 960. The sensors sub-module 963 comprises at least one of the devices, modules, and subsystems whose purpose is to detect events or changes in its environment and send the information to the computing device 900. Sensors are sensitive to the measured property, are not sensitive to any property not measured, but may be encountered in its application, and do not significantly influence the measured property. The sensors sub-module 963 may comprise a plurality of digital devices and analog devices, wherein if an analog device is used, an Analog to Digital (ADC, A-to-D) converter must be employed to interface the said device with the computing device 900. The sensors may be subject to a plurality of deviations that limit sensor accuracy. The sensors sub-module 963 may comprise a plurality of embodiments, such as, but not limited to, chemical sensors, automotive sensors, acoustic/sound/vibration sensors, electric current/electric potential/magnetic/radio sensors, environmental/weather/moisture/humidity sensors, flow/fluid velocity sensors, ionizing radiation/particle sensors, navigation sensors, position/angle/displacement/distance/speed/acceleration sensors, imaging/optical/light sensors, pressure sensors, force/density/level sensors, thermal/temperature sensors, and proximity/presence sensors.

Consistent with the embodiments of the present disclosure, the aforementioned computing device 900 may employ the peripherals sub-module 962 as a subset of the I/O 960. The peripheral sub-module 964 comprises ancillary devices uses to put information into and get information out of the computing device 900. There are 3 categories of devices comprising the peripheral sub-module 964, which exist based on their relationship with the computing device 900, input devices, output devices, and input/output devices. Input devices send at least one of data and instructions to the computing device 900. Input devices can be categorized based on, but not limited to:

Modality of input such as, but not limited to, mechanical motion, audio, and visual.

Whether the input is discrete, such as but not limited to, pressing a key, or continuous such as, but not limited to, the position of a mouse.

The number of degrees of freedom involved such as, but not limited to, two-dimensional mice vs three-dimensional mice used for Computer-Aided Design (CAD) applications.

Output devices provide output from the computing device 900. Output devices convert electronically generated information into a form that can be presented to humans. Input/output devices perform that perform both input and output functions.

Audio input devices are used to capture sound. In some cases, an audio output device can be used as an input device, in order to capture produced sound. Audio input devices allow a user to send audio signals to the computing device 900 for at least one of processing, recording, and carrying out commands. Devices such as microphones allow users to speak to the computer in order to record a voice message or navigate software. Aside from recording, audio input devices are also used with speech recognition software. Examples of types of audio input devices include, but not limited to microphone, Musical Instrument Digital Interface (MIDI) devices such as, but not limited to a keyboard, and headset.

IV. ASPECTS

The following disclose various Aspects of the present disclosure. The various Aspects are not to be construed as patent claims unless the language of the Aspect appears as a patent claim. The Aspects describe various non-limiting embodiments of the present disclosure.

Aspect 1
1. An apparatus comprising:
   a. Two hollow U-shaped manifolds having holes located on their interior faces;
      i. Wherein the U-shaped manifolds are designed to receive the top and bottom sets of teeth into an interior of each corresponding U-shaped manifold;
      ii. Wherein the holes are used for providing fluid jets;
         1. Wherein the holes are aligned towards the lingual and buccal side of the teeth for staggered arrangement of the jets;
      iii. Wherein the U-shaped manifolds may be connected, at a central point of reflection, by a rotating inlet joint which supplies the fluid for the jets;
   b. A design enabling dental irrigation with a controlled fluid flow by moving the apparatus in a sweeping motion between each set of rear molars.
2. The apparatus of aspect 1, with motive force applied to gums to translate the apparatus around a mouth.
3. The apparatus of aspect 1, wherein the rotating inlet joint encompasses an anti-rotate feature for the U-shaped manifolds.
4. The apparatus of aspect 1, wherein the U-shaped manifolds comprise a protruding soft membrane.
5. The apparatus of aspect 1, wherein the rotating inlet joint is used for the control mechanism for alternating jets between the faces of the U-shaped manifolds based on the position of the apparatus inside a mouth.
6. The apparatus of aspect 5, wherein a user may configure a method of alteration.
7. The apparatus of aspect 1, wherein the rotating inlet joint is used for the control of fluid pressure based on the position of the apparatus inside a mouth.
8. The apparatus of aspect 1, wherein the rotating inlet joint comprises a revolver that alternates jets between each U-shaped manifold surface.
9. The apparatus of aspect 1, wherein the extremities of the apparatus have electromagnetic wave sources attached.
10. The apparatus of aspect 1, wherein the interiors of the U-shaped manifolds have toothbrush bristles attached.
11. The apparatus of aspect 1, wherein the extremities of the apparatus have electromagnetic wave capturing devices attached.

Aspect 2
1. An apparatus for dental irrigation, the apparatus comprising:
a first manifold having a first plurality of outlet holes laid out on a first wall of the first manifold and a second wall of the first manifold, wherein the first wall approximately faces the second wall, and wherein the first plurality of outlet holes on the first wall of the first manifold are approximately oriented towards the first plurality of outlet holes on the second wall of the first manifold;

a second manifold having a second plurality of outlet holes laid out on a first wall of the second manifold and a second wall of the second manifold, wherein the first wall approximately faces the second wall, wherein the second plurality of holes on the first wall of the second manifold are approximately oriented towards the second plurality of holes on the second wall of the second manifold, and wherein the first manifold and the second manifold are positioned so as to approximately:
align with an approximately common axis of symmetry, and
reflect about a central point of reflection, such that each manifold is oriented in opposite directions; and a rotating inlet joint comprising an inlet channel to receive fluid at a first substantially perpendicular junction, wherein the substantially perpendicular junction is configured to channel the fluid into first and second substantially opposed directions:
the first direction towards the first manifold, and
the opposed second direction towards the second manifold,
wherein the rotating inlet joint is positioned in between the first manifold and the second manifold,
wherein the rotating inlet joint connects to the first manifold at a first inlet portion at approximately a base of the first manifold, the first inlet portion comprising a second substantially perpendicular junction at the base of the first manifold, the second substantially perpendicular junction being configured to receive the first direction fluid flow from the first substantially perpendicular junction, and direct said fluid flow in substantially opposing directions within the base portion of the first manifold, the opposing directions being substantially perpendicular to the first direction,
wherein the rotating inlet joint connects to the second manifold at a second inlet portion at approximately a base of the second manifold, the second inlet portion comprising a third substantially perpendicular junction at the base of the second manifold, the third substantially perpendicular junction being configured to receive the second direction fluid flow from the first substantially perpendicular junction, and direct said fluid flow in substantially opposing directions within the base portion of the second manifold, the opposing directions being substantially perpendicular to the second direction,
wherein the inlet channel of the rotating inlet joint protrudes from the rotating inlet joint to form an angle relative to the axis of symmetry,
wherein the rotating inlet joint is configured to rotate about the axis of symmetry to enable the inlet channel to turn about the axis of symmetry without blocking a flow of the fluid from the inlet channel to the first manifold and the second manifold, and
wherein the rotating inlet joint is configured to enable the flow of the fluid into the first manifold and the second manifold from the inlet channel at any angle of rotation about the axis of symmetry.

2. The apparatus of aspect 1, wherein the first manifold is configured to receive a user's upper teeth, wherein the second manifold is configured to receive the user's lower teeth, and wherein the rotating inlet joint is designed to accommodate the user's teeth arrangement by a location of the first inlet portion of the first manifold and the second inlet portion of the second manifold.

3. The apparatus of aspect 2, wherein a combined design of the first manifold, the second manifold, and the rotating inlet joint enables the user to sweep the apparatus from one side of the user's mouth to the other side of the user's mouth while the user's teeth are within each corresponding manifold.

4. The apparatus of aspect 3, wherein the rotating inlet joint is configured to rotate about the axis of symmetry as the user sweeps the first manifold and the second manifold within the user's mouth, without obstructing the flow of fluid from the inlet channel to the first plurality of outlet holes and the second plurality of holes.

5. The apparatus of aspect 1, wherein the first plurality of outlet holes and the second plurality of holes are configured to expel the fluid to form jets.

6. The apparatus of aspect 5, wherein the jets formed from the first wall of each manifold are arranged to be offset from the jets formed from the second wall of each manifold.

7. The apparatus of aspect 1, wherein the fluid flow alternates between the first manifold and the second manifold.

8. The apparatus of aspect 1, wherein the fluid flow alternates from the first wall of each manifold to the second wall of each manifold.

9. The apparatus of aspect 7, wherein the alternating fluid flow is provided by a flow alternating part.

10. The apparatus of aspect 9, wherein the part is mounted inside the rotating inlet joint between the first manifold and the second manifold.

11. The apparatus of aspect 10, wherein the part comprises a blower wheel, having fins which, when interfacing with a fluid flow, cause the part to rotate.

12. The apparatus of aspect 11, wherein the rotating inlet joint comprises an offset wall to divert the fluid flow, spinning the blower wheel in a particular direction.

13. The apparatus of aspect 11, wherein the part is divided into four quadrants, such that quadrant one and quadrant three block upward fluid flow, allowing downward fluid flow, and quadrant two and quadrant four block the downward fluid flow, allowing the upward fluid flow.

14. The apparatus of aspect 13, wherein each manifold comprises cutouts for each channel of the fluid flow corresponding to openings designed within the part, such that, as the part rotates, the part's openings align, in alternating fashion, with the cutouts of each manifold, thereby enabling each channel of the fluid flow into each manifold.

15. The apparatus of aspect 14, wherein the part is divided into the four quadrants, such that quadrant one and quadrant three block the fluid flow to the first manifold while allowing the fluid flow to the second manifold, and quadrant two and quadrant four block the fluid flow to the second manifold while allowing the fluid flow to the first manifold.

16. The apparatus of aspect 11, wherein the part is divided into two halves, such that a first half blocks upward fluid flow, allowing downward fluid flow, and a second half blocks the downward fluid flow, allowing the upward fluid flow.

17. The apparatus of aspect 16, wherein each manifold comprises two cutouts for fluid flow corresponding to the part halves, such that the two cutouts provide the fluid flow to the corresponding buccal and lingual sides of each manifold.
18. The apparatus of aspect 17, wherein, as the part spins, an open half of the part lines up with the first inlet portion of the first manifold and the second inlet portion of the second manifold, in sequence, providing an alternating upward and downward fluid flow to the corresponding buccal and lingual side of each manifold.
19. The apparatus of aspect 11, wherein fluid pressure determines the rate of spin for the part.
20. The apparatus of aspect 1, wherein a spring is mounted inside the rotating inlet joint, applying opposing pressure to the first manifold and the second manifold, wherein the spring enables a range of motion between the first manifold and the second manifold, such that the first manifold may be configured to move closer to, and further away from, the second manifold.
21. The apparatus of aspect 20, wherein the spring decompresses as fluid flow increases pressure within the rotating inlet joint.
22. The apparatus of aspect 20, wherein the spring compresses when a user provides pressure to the first manifold with upper teeth and the second manifold with lower teeth.
23. The apparatus of aspect 22, wherein a compression of the spring improves an alignment of the user's teeth within each manifold.
24. The apparatus of aspect 1, further comprising at least one roller having a motive force applied to a user's gums to translate the apparatus around the user's mouth.
25. The apparatus of aspect 24, further comprising a first roller directed towards the user's upper gum-line, and a second roller directed towards a user's lower gum-line.
26. An apparatus for dental irrigation designed to project fluid directly onto surfaces of, and interproximal spaces between, a user's teeth and gum-line, the apparatus comprising:
a rotating inlet joint comprising:
an inlet channel configured to receive the fluid,
a first substantially perpendicular junction comprising:
a first portion connecting to the inlet channel substantially perpendicularly towards a second portion, and
the second portion configured to channel the received fluid into first and second substantially opposed directions:
the first direction towards a first approximately U-shaped manifold via a first inlet portion of the first approximately U-shaped manifold, and
the second direction towards a second approximately U-shaped manifold via a second inlet portion of the second approximately U-shaped manifold,
wherein the rotating inlet joint is configured to rotate about an axis of rotation to enable the inlet channel to turn without blocking a flow of the fluid from the inlet channel to the first approximately U-shaped manifold and the second approximately U-shaped manifold, and
wherein the rotating inlet joint is configured to enable the flow of the fluid into the first approximately U-shaped manifold and the second approximately U-shaped manifold from the inlet channel at any angle of rotation about the axis of rotation;
the first approximately U-shaped manifold comprising:
the first inlet portion at approximately a base of the first approximately U-shaped manifold, the first inlet portion comprising a second substantially perpendicular junction at the base of the first approximately U-shaped manifold, the second substantially perpendicular junction being:
formed by a hollow interior portion of the first approximately U-shaped manifold, and
configured to:
receive the first direction fluid flow from the second portion of the first substantially perpendicular junction, and
direct said fluid flow in substantially opposing directions within the base portion of the first approximately U-shaped manifold,
a first plurality of outlet holes located on a first interior face of the first approximately U-shaped manifold, and
a second plurality of outlet holes located on a second interior face of the first approximately U-shaped manifold; and
the second approximately U-shaped manifold comprising:
the second inlet portion at approximately a base of the second approximately U-shaped manifold, the second inlet portion comprising a third substantially perpendicular junction at the base of the second approximately U-shaped manifold, the third substantially perpendicular junction being:
formed by a hollow interior portion of the second approximately U-shaped manifold, and
configured to:
receive the second direction fluid flow from the second portion of first substantially perpendicular junction, and
direct said fluid flow in substantially opposing directions at the base portion of the second approximately U-shaped manifold,
a third plurality of outlet holes located on a first interior face of the second approximately U-shaped manifold, and
a fourth plurality of outlet holes located on a second interior face of the second approximately U-shaped manifold.
27. The apparatus of aspect 26, wherein the first plurality of outlet holes of the first interior face of the first U-shaped manifold are asymmetrically aligned relative to the second plurality of outlet holes on the second interior face of the first U-shaped manifold.
28. The apparatus of aspect 26, wherein the third plurality of outlet holes of the first interior face of the second approximately U-shaped manifold are asymmetrically aligned relative to the fourth plurality of outlet holes on the second interior face of the second approximately U-shaped manifold.
29. The apparatus of aspect 26, wherein the rotating inlet joint connects the first approximately U-shaped manifold and the second approximately U-shaped manifold to form an approximately H-shaped manifold, and wherein the approximately H-shaped manifold is configured to channel the fluid received from the inlet channel to the first plurality of outlet holes, the second plurality of outlet holes, the third plurality of outlet holes, and the fourth plurality of outlet holes, and wherein the rotating inlet joint is configured to rotate about an approximately vertical axis of symmetry of the approximately H-shaped manifold to enable the inlet channel to turn about a vertical axis of symmetry without:
altering a position of the first approximately U-shaped manifold and the position of the second approximately U-shaped manifold.

30. An apparatus for dental irrigation designed to project fluid directly onto surfaces of, and interproximal spaces between, a user's teeth and gum-line, the apparatus comprising:
a first manifold segment comprising:
a first arm having a first plurality of outlet holes, the first plurality of outlet holes providing an opening into a hollow interior of the first arm,
a second arm having a second plurality of outlet holes, the second plurality of outlet holes providing an opening into a hollow interior of the second arm, and
a first base portion comprising at least one first inlet, wherein a hollow interior of the first base portion forms a first substantially perpendicular junction, the first substantially perpendicular junction being configured to receive the fluid from the at least one first inlet and channel the fluid, within the first base portion of the first manifold segment, in opposing directions,
wherein a first direction of the opposing directions of fluid flow provided by the first substantially perpendicular junction leads to the hollow interior of the first arm and a second direction of the opposing directions of fluid flow provided by the first substantially perpendicular junction leads to the hollow interior of the second arm,
a second manifold segment comprising:
a third arm having a third plurality of outlet holes, the third plurality of outlet holes providing an opening into a hollow interior of the third arm,
a fourth arm having a fourth plurality of outlet holes, the fourth plurality of outlet holes providing an opening into a hollow interior of the fourth arm, and
a second base portion comprising at least one second inlet,
wherein a hollow interior of the second base portion forms a second substantially perpendicular junction, the second substantially perpendicular junction being configured to receive the fluid from the at least one second inlet and channel the fluid, within the second base portion of the second manifold segment, in opposing directions,
wherein a first direction of the opposing directions of fluid flow provided by the first substantially perpendicular junction leads to the hollow interior of the third arm and a second direction of the opposing directions of fluid flow provided by the second substantially perpendicular junction leads to the hollow interior of the fourth arm; and
a rotating inlet segment comprising an inlet channel to receive the fluid and channel the fluid in a first direction, into the first manifold segment through a first inlet and into the second manifold segment through a second inlet;
wherein the rotating inlet segment, the first manifold segment, and the second manifold segment are positioned so as to approximately:
align with an approximately central vertical axis of symmetry, and
reflect about an approximately central horizontal axis of symmetry, such that the first manifold segment and the second manifold segment are positioned at opposite sides of the rotating inlet segment and are oriented in opposite directions, and
wherein the rotating inlet segment is configured to rotate about the vertical axis of symmetry to enable the inlet channel to turn about the vertical axis of symmetry without blocking the fluid flow from the inlet channel to the first manifold segment and the second manifold segment, and
wherein the rotating inlet segment is configured to enable the fluid flow into the first manifold segment and the second manifold segment from the inlet channel at any angle of rotation about the vertical axis symmetry.

V. CLAIMS

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as example for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The invention claimed is:
1. An apparatus for dental irrigation, the apparatus comprising:
a first manifold including a first shell having an inner portion and an outer portion, the first shell having a first set of one or more outlets in a first substantially planar wall and a second set of one or more outlets in a second substantially planar wall, wherein at least one of the first wall and the second wall is capable of contacting a user's tooth, wherein the first wall approximately faces the second wall, and wherein at least a portion of the first manifold is shaped to accommodate a tooth and configured to glide across a plurality of teeth in a user's dental arch;
a second manifold including a second shell having an inner portion and an outer portion, the second shell having a third set of one or more outlets in a third wall and a fourth set of one or more outlets in a fourth wall, wherein at least one of the third wall and the fourth wall is capable of contacting a user's tooth, wherein the third substantially planar wall approximately faces the fourth substantially planar wall, and wherein at least a portion of the second manifold is shaped to accommodate a tooth and configured to glide across a plurality of teeth in the user's dental arch; and
a rotating inlet joint comprising an inlet channel and a rotating joint, the rotating inlet joint being configured to enable a flow of a fluid into the first manifold and the second manifold from the inlet channel at any angle of rotation about an axis of rotation defined by the rotating joint;
wherein the first set of one or more outlets and the second set of one or more outlets are oriented towards a tooth accommodated by the first manifold and gums associated with the tooth;

wherein the third set of one or more outlets and the fourth set of one or more outlets are oriented towards a tooth accommodated by the second manifold and gums associated with the tooth;
wherein the inner portion and the outer portion of the first shell cooperate to direct fluid flow substantially horizontal to the fluid flow exiting the inlet channel, and then substantially perpendicular to the fluid flow exiting the inlet channel, and
wherein the inner portion and the outer portion of the second shell cooperate to direct fluid flow substantially horizontal to the fluid flow exiting then inlet channel, and then substantially perpendicular to the fluid flow exiting the inlet channel.

2. The apparatus of claim 1, wherein at least a portion of the inlet channel of the rotating inlet joint protrudes from the rotating inlet joint to form an angle relative to the axis of rotation.

3. The apparatus of claim 2, wherein the angle of rotation impacts a property of the fluid flow to a user's teeth and associated gums;
wherein the impacted property comprises a rate of fluid flow, and wherein the impact is a reduction of the rate.

4. The apparatus of claim 1, wherein the first manifold and the second manifold have a fixed orientation relative to one another.

5. The apparatus of claim 1, wherein the rotating inlet joint is disposed between the first manifold and the second manifold.

6. The apparatus of claim 5, wherein the rotating inlet joint channels the fluid in substantially opposing directions into:
the first manifold towards the first set of one or more outlets and the second set of one or more outlets, such that the fluid is channeled to be expelled from the first set of one or more outlets and the second set of one or more outlets, and
the second manifold towards the third set of one or more outlets and the fourth set of one or more outlets, such that the fluid is channeled to be expelled from the third set of one or more outlets and the fourth set of one or more outlets.

7. An apparatus for dental irrigation, the apparatus comprising:
a first manifold having a first set of one or more outlets laid out on a first substantially planar wall of the first manifold and a second set of one or more outlets laid out on a second substantially planar wall of the first manifold, and at least one first inlet, wherein at least one of the first wall and the second wall is capable of contacting a user's tooth, and wherein at least a portion of the first manifold being shaped to accommodate a tooth and configured to glide across a plurality of teeth in a user's dental arch;
a second manifold having a third set of one or more outlets laid out on a first substantially planar wall of the second manifold and a fourth set of one or more outlets laid out on a second substantially planar wall of the second manifold, and at least one second inlet, wherein at least one of the first wall and the second wall is capable of contacting a user's tooth, and wherein at least a portion of the second manifold being shaped to accommodate a tooth and configured to glide across a plurality of teeth in the user's dental arch; and
a rotating inlet joint comprising an inlet channel to receive fluid and a rotating joint to channel the fluid in substantially opposing directions into the first manifold through the at least one first inlet, and into the second manifold through the at least one second inlet,
wherein the rotating inlet joint, the first manifold, and the second manifold are positioned so as to approximately align with an approximately central vertical axis of common symmetry, and reflect about an approximately central horizontal axis of symmetry, such that the first manifold and the second manifold are positioned at opposite sides of the rotating inlet joint and are oriented in opposite directions, and
wherein the first manifold and the second manifold rotate about the axis of common symmetry;
wherein the rotating inlet joint is configured to rotate about the axis of common symmetry, and wherein the angle of rotation of the rotating inlet joint about the axis of common symmetry impacts a property of the fluid flow to a user's teeth and associated gums.

8. The apparatus of claim 7, wherein at least a portion of the inlet channel of the rotating inlet joint protrudes from the rotating inlet joint to form an angle relative to the axis of common symmetry.

9. The apparatus of claim 8, wherein the rotating inlet joint is configured to rotate fully about the axis of common symmetry.

10. The apparatus of claim 7, wherein the first manifold and the second manifold have a fixed orientation relative to one another.

11. The apparatus of claim 7, wherein the rotating inlet joint is disposed between the first manifold and the second manifold.

12. The apparatus of claim 11, wherein the rotating inlet joint channels the fluid in substantially opposing directions into:
the first manifold towards the first set of one or more outlets and the second set of one or more outlets, such that the fluid is channeled to be expelled from the first set of one or more outlets and the second set of one or more outlets, and
the second manifold towards the third set of one or more outlets and the fourth set of one or more outlets, such that the fluid is channeled to be expelled from the third set of one or more outlets and the fourth set of one or more outlets.

13. The apparatus of claim 7,
wherein the first set of one or more outlets and the second set of one or more outlets are oriented towards a tooth accommodated by the first manifold and gums associated with the tooth; and
wherein the third set of one or more outlets and the fourth set of one or more outlets are oriented towards a tooth accommodated by the second manifold and gums associated with the tooth.

14. An apparatus for dental irrigation, the apparatus comprising:
a first manifold including a first shell having an inner portion and an outer portion, the first shell having a first set of one or more outlets laid out on a first substantially planar wall and a second set of one or more outlets laid out on a second substantially planar wall, wherein the first wall approximately faces the second wall,
wherein at least one of the first wall and the second wall is capable of contacting a user's tooth;
wherein at least a portion of the first manifold further is shaped to accommodate a tooth and configured to glide across a plurality of teeth in a user's dental arch;

a rotating inlet joint configured to enable a flow of a fluid into the first manifold from an inlet channel at any angle of rotation about an axis of rotation;

wherein the inner portion and the outer portion of the first shell cooperate to direct the fluid flow substantially perpendicularly to the fluid flow exiting the inlet channel, and then substantially parallel to the fluid flow exiting the inlet channel, then substantially perpendicularly again.

15. The apparatus of claim 14, wherein the first set of one or more outlets and the second set of one or more outlets are oriented towards a tooth accommodated by the first manifold and gums associated with the tooth.

16. The apparatus of claim 14, further comprising a second manifold that mirrors the first manifold, reflected about a horizontal axis of symmetry, the second manifold including a second shell having an inner portion and an outer portion, the second shell having a third set of one or more outlets laid out on a third substantially planar wall and a fourth set of one or more outlets laid out on a fourth substantially planar wall, wherein at least one of the first wall and the second wall is capable of contacting a user's tooth, and wherein at least a portion of the second manifold is shaped to accommodate a tooth and configured to glide along a plurality of teeth in the user's dental arch, wherein the third wall approximately faces the fourth wall, wherein the third set of one or more outlets and the fourth set of one or more outlets are oriented towards a tooth accommodated by the second manifold and gums associated with the tooth;

wherein the rotating inlet joint is further configured to enable a flow of the fluid into the second manifold from the inlet channel at any angle of rotation about the axis of rotation; and wherein the inner portion and the outer portion of the second shell cooperate to direct the fluid flow substantially perpendicularly to the fluid flow exiting the inlet channel, and then substantially horizontal to the fluid flow exiting the inlet channel, then substantially perpendicularly again.

17. The apparatus of claim 14, wherein at least a portion of the inlet channel of the rotating inlet joint protrudes from the rotating inlet joint to form an angle relative to the axis of rotation.

18. The apparatus of claim 17, wherein the angle impacts a property of the fluid flow to a user's teeth and associated gums.

19. The apparatus of claim 16, wherein the first manifold and the second manifold have a fixed orientation relative to one another.

20. The apparatus of claim 16, wherein the rotating inlet joint is disposed between the first manifold and the second manifold.

* * * * *